(12) United States Patent
Takeda et al.

(10) Patent No.: US 11,725,179 B2
(45) Date of Patent: Aug. 15, 2023

(54) SINGLE-PARTICLE ANALYSIS METHOD, AND SYSTEM FOR PERFORMING SAID ANALYSIS

(71) Applicant: ON-CHIP BIOTECHNOLOGIES CO., LTD., Tokyo (JP)

(72) Inventors: Kazuo Takeda, Tokyo (JP); Yuu Fujimura, Tokyo (JP); Takahide Ino, Tokyo (JP); Masayuki Ishige, Tokyo (JP); Jin Akagi, Tokyo (JP)

(73) Assignee: ON-CHIP BIOTECHNOLOGIES CO., LTD., Tokyo (JP)

( * ) Notice: Subject to any disclaimer, the term of this patent is extended or adjusted under 35 U.S.C. 154(b) by 556 days.

(21) Appl. No.: 15/573,459

(22) PCT Filed: May 12, 2016

(86) PCT No.: PCT/JP2016/064196
§ 371 (c)(1),
(2) Date: Apr. 9, 2018

(87) PCT Pub. No.: WO2016/182034
PCT Pub. Date: Nov. 17, 2016

(65) Prior Publication Data
US 2018/0298324 A1    Oct. 18, 2018

(30) Foreign Application Priority Data
May 12, 2015    (JP) .................. 2015-097758

(51) Int. Cl.
*C12Q 1/68*    (2018.01)
*C12M 1/00*    (2006.01)
(Continued)

(52) U.S. Cl.
CPC ....... *C12M 47/04* (2013.01); *B01L 3/502761* (2013.01); *B01L 3/502784* (2013.01);
(Continued)

(58) Field of Classification Search
None
See application file for complete search history.

(56) References Cited

U.S. PATENT DOCUMENTS 3,710,933 A    1/1973    Fulwyler
3,826,364 A    7/1974    Bonnner
(Continued)

FOREIGN PATENT DOCUMENTS

CN    1973195 A    5/2007
CN    101189504    5/2008
(Continued)

OTHER PUBLICATIONS

Bert Vogelstein and Kenneth W. Kinzler, "Digital PCR", Proc. Natl. Acad. Sci. USA, vol. 96, pp. 9236-9241, Aug. 1999.
(Continued)

*Primary Examiner* — Aaron A Priest
(74) *Attorney, Agent, or Firm* — Heslin Rothenberg Farley & Mesiti PC; Jacquelyn A. Graff, Esq.

(57) ABSTRACT

An object of the present invention is to purify and concentrate differentiating cells derived from ES cells, iPS cells, or the like without damaging them.
The above problem can be solved by an apparatus for analyzing and separating particles comprising: a flow path cartridge, an illumination unit, a detection unit for detecting particles of interest, a force generating unit, wherein a sample liquid reservoir (sample reservoir) connected to a first flow path; a fourth branched flow path and a fifth branched flow path which are connected to the first flow path; a third-A reservoir connected to the fourth branched flow path; a third-B reservoir connected to the fifth branched flow path; and a fourth reservoir for reserving particles which are not sorting; are formed on the cartridge, and each reservoir comprise a means which equalizes an air pressure in the each reservoir with an air pressure of an
(Continued)

in-device air pressure control system, and a stream of the flow path in the cartridge is controlled by controlling the air pressure in the each reservoir through the each in-device air pressure control system.

5 Claims, 15 Drawing Sheets

(51) Int. Cl.
$$
\begin{array}{ll}
C12N\ 5/07 & (2010.01) \\
C12Q\ 1/02 & (2006.01) \\
G01N\ 15/14 & (2006.01) \\
B01L\ 3/00 & (2006.01) \\
C12M\ 1/32 & (2006.01) \\
C12M\ 1/26 & (2006.01) \\
C12M\ 1/34 & (2006.01) \\
C12Q\ 1/6881 & (2018.01) \\
G01N\ 15/10 & (2006.01)
\end{array}
$$

(52) U.S. Cl.
CPC .............. *C12M 1/00* (2013.01); *C12M 23/12* (2013.01); *C12M 33/04* (2013.01); *C12M 41/46* (2013.01); *C12M 47/06* (2013.01); *C12N 5/06* (2013.01); *C12Q 1/02* (2013.01); *C12Q 1/6881* (2013.01); *G01N 15/1404* (2013.01); *G01N 15/1434* (2013.01); *G01N 15/1484* (2013.01); *B01L 2200/0652* (2013.01); *B01L 2200/0673* (2013.01); *B01L 2300/0861* (2013.01); *B01L 2400/0481* (2013.01); *B01L 2400/0487* (2013.01); *G01N 15/1459* (2013.01); *G01N 2015/1006* (2013.01); *G01N 2015/149* (2013.01)

(56) References Cited

U.S. PATENT DOCUMENTS

| | | | |
|---|---|---|---|
| 4,756,427 | A | 7/1988 | Gohde |
| 6,657,713 | B2 | 12/2003 | Hansen |
| 6,808,075 | B2 | 10/2004 | Bohm |
| 7,968,287 | B2 | 6/2011 | Griffiths |
| 8,248,604 | B2 | 8/2012 | Takeda |
| 8,822,207 | B2 | 9/2014 | Foster |
| 8,834,793 | B2 | 9/2014 | Koltay |
| 8,993,311 | B2 | 3/2015 | Foster |
| 2005/0136528 | A1 | 6/2005 | Bahnson |
| 2006/0141618 | A1 | 6/2006 | Yasuda |
| 2007/0065808 | A1* | 3/2007 | Bohm ............... B01L 3/502761 435/4 |
| 2008/0257072 | A1 | 10/2008 | Takahashi |
| 2009/0129985 | A1 | 5/2009 | Ikushima |
| 2010/0123457 | A1 | 5/2010 | Shinoda |
| 2011/0294139 | A1 | 12/2011 | Takeda |
| 2012/0160017 | A1 | 6/2012 | Shen |
| 2012/0288920 | A1* | 11/2012 | Takeda ............... G01N 15/1484 435/286.5 |
| 2014/0370511 | A1 | 12/2014 | Katasho et al. |
| 2015/0056607 | A1 | 2/2015 | Jooris et al. |
| 2015/0057163 | A1 | 2/2015 | Rotem |

FOREIGN PATENT DOCUMENTS

| | | |
|---|---|---|
| CN | 101893569 | 11/2010 |
| CN | 102077071 | 5/2011 |
| CN | 101419171 | 1/2012 |
| CN | 102393473 | 3/2012 |
| CN | 102533536 | 7/2012 |
| CN | 103069266 | 4/2013 |
| CN | 104204767 | 12/2014 |
| JP | 643541 | 1/1989 |
| JP | 1170853 | 5/1989 |
| JP | 1170853 | 7/1989 |
| JP | 643541 | 9/1989 |
| JP | 02051044 | 2/1990 |
| JP | 11295323 | 10/1999 |
| JP | 2001120261 | 5/2001 |
| JP | 2005524831 | 8/2005 |
| JP | 2006300565 | 11/2006 |
| JP | 2010151777 | 7/2010 |
| JP | 2011512825 | 4/2011 |
| JP | 2012080819 | 4/2012 |
| JP | 4927719 | 5/2012 |
| JP | 2012165699 | 9/2012 |
| JP | 2013130548 | 7/2013 |
| JP | 5382852 | 8/2014 |
| WO | 1996028732 | 9/1996 |
| WO | 1998010267 | 3/1998 |
| WO | 2003089158 | 10/2003 |
| WO | 2004101731 | 11/2004 |
| WO | 2006076195 | 7/2006 |
| WO | 2009109368 | 9/2009 |
| WO | 2012021458 | 2/2012 |
| WO | 2011086990 | 5/2013 |

OTHER PUBLICATIONS

White et al., "Digital PCR provides sensitive and absolute calibration for high throughput sequencing", BMC Genomics, 2009; 10:116.

Jim F. Huggett et al., "The Digital MIQE Guidelines: Minimum Information for Publication of Quantitative Digital PCR", Clinical Chemistry, Jun. 2013; 59(6):892-902.

Nao Hirata et al., "A Chemical Probe that Labels Human Pluripotent Stem Cells", Cell Reports 6, 1165-1174, Mar. 27, 2014.

Richard Williams et al., "Amplification of complex gene libraries by emulsion PCR", Nature Methods, vol. 3, No. 7, 2006, pp. 545-550.

Sigma-Aldrich Product Information, SeqPlex DNA Amplification Kit Catalog No. SEQXE, 2014.

Sigma-Aldrich Product Information, SeqPlex RNA Amplification Kit Catalog No. SEQR, 2014.

International Search Report for PCT/JP2016/064196 dated Aug. 9, 2016, 8 pages.

\* cited by examiner (A)
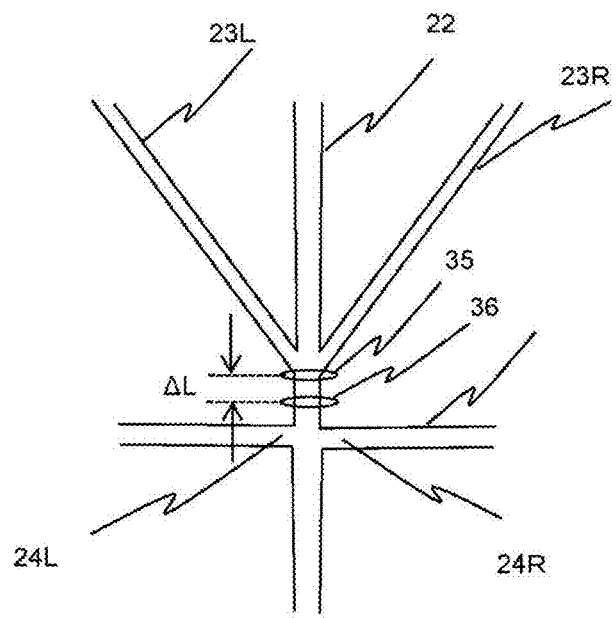
(B)
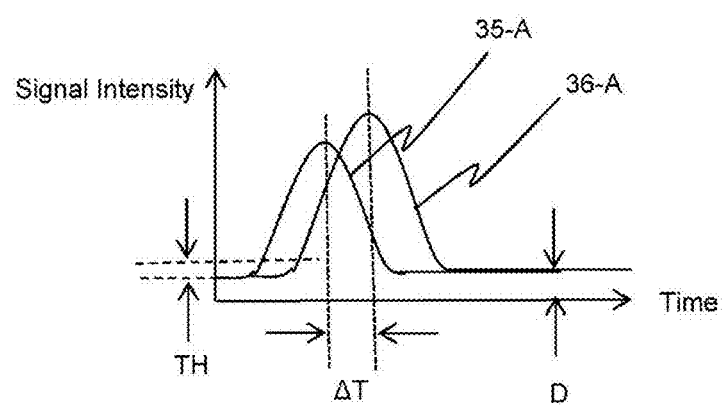
FIG. 5

Sectional view along BB' of Fig.2

(A)
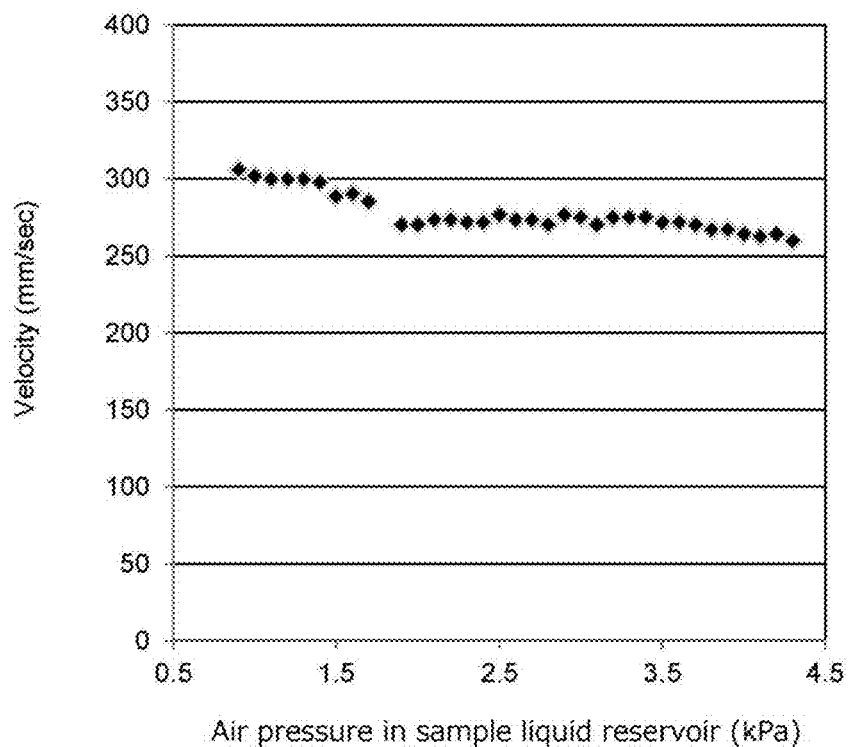
(B)
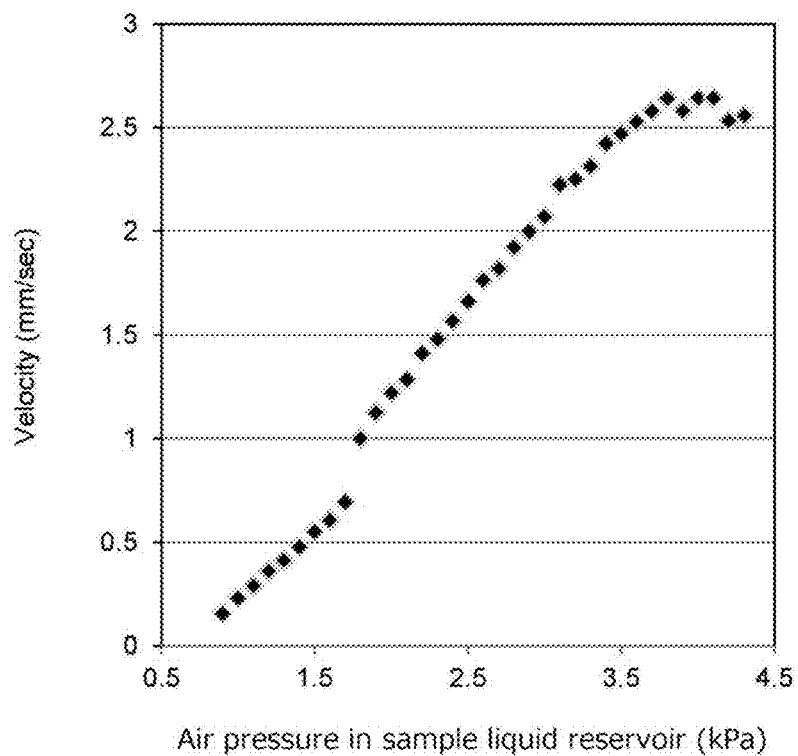
FIG. 12

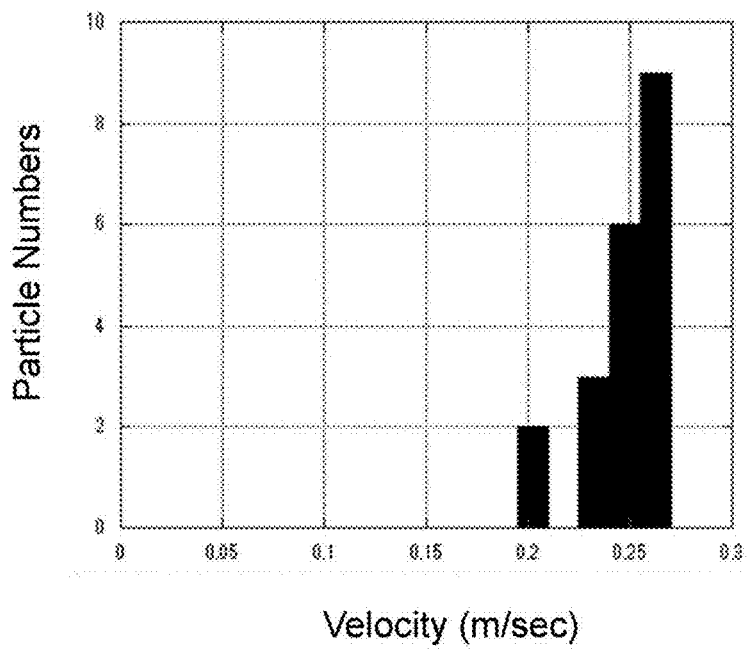

FIG. 14

(A) Actual measured result and simulation result of removal efficiency when undifferation cell ratio is 20%

| | After first treatment(60min) | | After second treatment(40min) | | After third treatment(30min) | | After forth treatment(20min) | |
|---|---|---|---|---|---|---|---|---|
| | Collection number | Undifferation ratio | Collection number | Undifferation ratio | Collection number | Undifferation ratio | Collection number | Undifferation ratio |
| Actual measurement | 1.6×10^6 | 7% | 1.2×10^6 | 1% | 7.2×10^5 | 0.078% (560 cells) | 5.0×10^5 | 0% (0 cell) |
| Simulation | 1.7×10^6 | 4.9% | 1.5×10^6 | 0.68% | 1.2×10^6 | 0.010% (120 cells) | 7.2×10^5 | 0.00005% (0 cell) |

(B) Simulation result of removal efficiency when undifferation cell ratio is 0.3% or less

| Sample condition | | After first treatment | | After second treatment | | After third treatment | |
|---|---|---|---|---|---|---|---|
| Cell number | Undifferation ratio % (number) | Removal ratio% (Remained undifferation cell number) | Collection ratio% (Collection number) | Removal ratio% (Remained undifferation cell number) | Collection ratio% (Collection number) | Removal ratio% (Remained undifferation cell number) | Collection ratio% (Collection number) |
| 10^7 | 0.1 (10000) | 99.79 (20.83 cells) | 85 (0.85×10^7 cells) | 99.999998 (≈0 cells) | 85 (0.85×10^7 cells) | 100 (≈0 cells) | 85 (0.85×10^7 cells) |
| | 0.2 (20000) | 99.59 (83 cells) | 71 (0.71×10^7 cells) | 99.999998 (≈0 cells) | 71 (0.71×10^7 cells) | 100 (≈0 cells) | 71 (0.71×10^7 cells) |
| | 0.3 (30000) | 99.39 (182 cells) | 58 (0.58×10^7 cells) | 99.9999 (≈0 cells) | 58 (0.58×10^7 cells) | 100 (≈0 cells) | 58 (0.58×10^7 cells) |
| 0.3×10^8 | 0.1 (30000) | 99.39 (182 cells) | 58 (0.58×10^7 cells) | 99.9999 (≈0 cells) | 58 (0.58×10^7 cells) | 100 (≈0 cells) | 58 (0.58×10^7 cells) |

FIG. 15

SINGLE-PARTICLE ANALYSIS METHOD, AND SYSTEM FOR PERFORMING SAID ANALYSIS

CROSS REFERENCE TO RELATED APPLICATIONS

This application is a national stage filing under section 371 of International Application No. PCT/JP2016/064196, filed on May 12, 2016, and published on Nov. 17, 2016 as WO 2016/182034, which claims priority to Japanese Application No. 2015/097758, filed May 12, 2015. The entire contents of each application are incorporated herein by reference in their entireties.

TECHNICAL FIELD

The present invention relates to a method for purifying and concentrating differentiating cells derived from ES cells or iPS cells of animals including humans, without damaging the same, and further relates to a method for sorting and analyzing cells or clump of cells (cell spheroids) one by one.

BACKGROUND ART

In a field of regenerative medicine, a technique for differentiating cells of interest is key in order to apply pluripotent stem cells to a regenerative medicine or drug discovery. In this regard, if undifferentiated cells are mixed in differentiating cells, it causes tumors to develop. Thus, a technique for completely removing them has become greatly important. Further, the removing treatment must be carried out aseptically. A concentration of specific cells is generally carried out through use of a cell sorter as explained below. However, it is not suitable for a technique of regenerative medicine, because the cell sorter is not aseptic and cells are subjected to heavy damage. Currently, therefore, a new apparatus suitable for an actual use is desired.

Firstly, a conventional cell sorter for sorting cells is explained. The cell sorter is an apparatus for sorting and concentrating cells of interest, and further has an analytical function of flow cytometry for identifying the cells of interest. Flow cytometers are typically used to identify various types of cells and particles included in a liquid. Flow cytometers of the related art have an optically transparent flow cell made of quartz, formed with a flow path through which a liquid containing the cells to be individually identified flow. Generally, the flow of cells passing through the flow path is concentrated in the center portion of the flow path by a sheath liquid concentrically surrounding the flow of cells. The center portion of the flow path is illuminated with a laser beam. When a cell passes through an illumination region, light is scattered depending on the size, shape, and refractive index of the cell. To detect a cell specifically dyed with a fluorescent dye by fluorescence, the wavelength of the laser beam is determined in accordance with the type of the fluorescent dye. In this manner, the fluorescence as well as the scattered light for each of the cells is detected by multiple photodetectors based on the wavelength, enabling a diverse analysis of the cell. Technique of flow cytometry is described in Patent literature 1.

Existing cell sorting methods will now be described. The method described in Patent literature 1 or Patent literature 2 is a separation method currently adopted in common products. The method includes discharging liquid droplets of a sample liquid from a nozzle for droplet formation into the air, and separating the liquid droplets which include the cells to be separated using an electric field. Patent literature 3 discloses a method that includes the steps of flowing a sheath flow at the periphery of a sample liquid flowing through a flow cell, and shifting charged particles from the sample flow to the sheath flow by applying an electric field to the sample liquid for separation and measurement. Patent literature 4 describes a method that includes a step of applying a pressure pulse to a particle flowing through a flow cell, and thus separating the particles into a flow path which is different from a flow path for steady flow in the flow cell. Patent literature 5 discloses a technique that includes applying a field to a flow of micro particles, the flow of which had been narrowed by a sheath flow in the flow cell, and shifting the flow of the micro particles for separation. Patent literature 6 discloses a method of using gel electrodes disposed on both sides of a liquid flow path in a flow cell to apply a charge to the cell and then using an electric field to separate the cell. Patent literature 7 discloses a method that includes the steps of applying a pressure pulse by using a bubble valve forming a meniscus perpendicularly with respect to the flow of particles, and shifting the flow for separation. Patent literature 8 discloses a method that includes a step of applying a pressure pulse as in Patent literature 5, but also includes steps of ejecting each droplet including target particles, and collecting them in a container. Patent literature 9 describes a method that includes steps of measuring each particle in a flow of sample liquid narrowed by a sheath flow, and if it is judged that the particle is a target particle, separating the particles to generate a pulse flow to shift them into a different flow path. This technique is a sorting technique for a fixed mount type micro-flow path, but not a sorting technique for a disposable micro-flow path. A method that includes using magnetic particles coated with an antibody, absorbing the magnetic particles to a particular cell, and separating it by a gradient magnetic field is known (Patent literature 10). Patent literature 11 describes a contamination-free technique of a flow cytometer using the disposable micro-flow path cartridge, which is most suitable for regenerative medicine. Further, Patent literature 12 describes a method for separating cells in the disposable micro-flow path cartridge. Furthermore, Patent literature 13 discloses an improved method in which an influence of flow in the micro-flow path is reduced. As the techniques for separating cells in the disposable micro-flow path chip, techniques wherein magnetically driven valves are equipped in a flow path so as to sort cells, are disclosed in Patent literature 14 and Patent literature 15.

Next, a technique for dispensing cells one by one is explained. Patent literature 16 discloses a technique wherein cells are picked up by a hollow pipette and moved to a different location, and then dispensed by being discharged. Patent literature 17 discloses a technique wherein each of the liquid droplets is delivered by drops through pressure pulse drive using a piezoelectric element and dispensed, after detecting a presence or absence of the cells by image recognition. Further, Patent literature 17 discloses a dispensing method wherein a dispensing head is disposable, in order to dispense aseptically.

Next, a technique capable of analyzing genes of cells one by one is explained. The technique called a digital PCR was advocated by Vogelstein and KINZLER in 1999. As a method for detecting a gene sequence of interest in contaminating substances at high sensitivity, this technique is superior, and described in Non-patent literature 1. In this technique, an influence of the contaminating substances is excluded by infinitesimally dividing an area of a PCR reaction, whereby it becomes possible to detect it with high sensitivity.

Patent literature 19 discloses the following techniques, i.e. a technique for forming emulsion of in-oil liquid droplets using fluorine oil, a technique for performing the digital PCR in the in-oil liquid droplets of emulsion, a method for adding another PCR reaction reagent to a droplet by a technique for fusing two emulsion droplets on a one-to-one level.

Patent literature 20 describes a technique for measuring a flow rate of particles passing through a flow path. In this technique, a single light source is divided into two courses, by which two positions with a certain separation in a flow direction are illuminated, and the flow rate is measured by a time lag between the two positions.

Patent literature 21 describes a method for collecting a particle of interest wherein a pulse wind is applied to an unwanted particle when the unwanted particle is flowed down into the air from a nozzle, to thereby blow away the unwanted particle, and the particle of interest is collected by dropping the same.

Patent literature 22 discloses a technique for forming in-oil liquid droplets containing cells, and further discloses a method for adding another PCR reaction reagent to a particle in emulsion by a technique for fusing two particles in emulsion on a one-to-one level.

CITATION LIST

Patent Literature

[PATENT LITERATURE 1] U.S. Pat. No. 3,710,933
[PATENT LITERATURE 2] U.S. Pat. No. 3,826,364
[PATENT LITERATURE 3] Japanese Unexamined Patent Publication (Kokai) No. 64-3541
[PATENT LITERATURE 4] Japanese Unexamined Patent Publication (Kokai) No. 1-170853
[PATENT LITERATURE 5] WO98/10267
[PATENT LITERATURE 6] WO2004/101731
[PATENT LITERATURE 7] U.S. Pat. No. 6,808,075
[PATENT LITERATURE 8] WO2006/076195
[PATENT LITERATURE 9] U.S. Pat. No. 4,756,427
[PATENT LITERATURE 10] WO96/28732
[PATENT LITERATURE 11] U.S. Pat. No. 8,248,604
[PATENT LITERATURE 12] Japanese Patent No. 5382852
[PATENT LITERATURE 13] WO2011/086990
[PATENT LITERATURE 14] U.S. Pat. No. 8,822,207
[PATENT LITERATURE 15] U.S. Pat. No. 8,993,311
[PATENT LITERATURE 16] U.S. Patent Publication No. 2005/0136528
[PATENT LITERATURE 17] U.S. Pat. No. 8,834,793
[PATENT LITERATURE 18] Japanese Patent No. 4927719
[PATENT LITERATURE 19] U.S. Pat. No. 7,968,287
[PATENT LITERATURE 20] Japanese Unexamined Patent Publication (Kokai) No. 2006-300565
[PATENT LITERATURE 21] U.S. Pat. No. 6,657,713
[PATENT LITERATURE 22] U.S. Patent Publication No. US20150057163
[PATENT LITERATURE 23] Japanese Unexamined Patent Publication (Kokai) No. 11-295323

Non-Patent Literature

[NON-PATENT LITERATURE 1] BERT VOGELSTEIN AND KENNETH W. KINZLER "Digital PCR" Proc. Natl. Acad. Sci. USA Vol. 96, pp. 9236-9241, August 1999
[NON-PATENT LITERATURE 2] White et al. "Digital PCR provides sensitive and absolute calibration for high throughput sequencing" BMC Genomics 2009; 10:116
[NON-PATENT LITERATURE 3] Jim F. Huggett et al. "The Digital MIQE Guidelines: Minimum Information for Publication of Quantitative Digital PCR" Clinical Chemistry 2013 June; 59(6):892-902.
[NON-PATENT LITERATURE 4] Nao Hirata et al. "A Chemical Probe that Labels Human Pluripotent Stem Cells" Cell Reports 6, 1165-1174, Mar. 27, 2014
[NON-PATENT LITERATURE 5] Richard Williams et al. "Amplification of complex gene libraries by emulsion PCR" NATURE METHODS VOL. 3 NO. 7 2006 545-550
[NON-PATENT LITERATURE 6] SIGMA-ALDRICH Product Information SeqPlex DNA Amplification Kit-Catalog Number: SEQXE
[NON-PATENT LITERATURE 7] SIGMA-ALDRICH Product Information SeqPlex RNA Amplification Kit-Catalog Number: SEQR

SUMMARY OF INVENTION

Technical Problem

Some problems in a cell analysis for the regenerative medicine will be described below.
1) Problem in Sorting Regarding the sorting suitable for regenerative medicine, the problems in the sorting technique using the disposable micro-flow path cartridge suitable for an aseptic sorting without contamination and damage is mainly explained.
1-1) Problem in the Sorting for the Aseptic Treatment Regarding the sorting treatment for regenerative medicine, it is required that the sorting treatment does not damage the sorted cells and the sorting treatment is aseptic. As the sorter meeting the above requirements, the sorting method in the disposable flow path cartridge is more suitable for the above requirements than the sorting method in the air. As the sorting method in the disposable flow path cartridge, Patent literature 13 discloses a sorting method wherein a cell flow in the flow path cartridge is controlled by an air pressure, to sorting cells. In this method, air in a reservoir on the flow path cartridge is connected to air in an air pump formed outside of the flow path cartridge, through a filter. The filter prevents a contamination of bacterium and extraneous substances with a liquid in the flow path cartridge. However, when a pore size of the filter is small, air conductance becomes low, and thus there is a problem in that it causes a reduction in the sorting force.

Patent literature 14 and Patent literature 15 disclose a technique for sorting cells wherein magnetically movable valves are equipped in a flow path of the disposable flow path cartridge and the valves are externally-driven by turning an electric magnet on or off to sort cells. In this case, the sorting force is a magnetic force which is different from the force of air, and thus the cells can be sorted in an enclosed space and an aseptic sorting can be carried out. However, complicated movable structures which are not suitable for a mass-production, are incorporated into the disposable flow path cartridge, and thus there is a problem of an expensiveness thereof.
1-2) Problem in Adjustment of Sample Concentration Patent literature 11 discloses a technique of a flow cytometry using the disposable flow path cartridge. In this technique, an identical air pressure is applied to a sheath liquid reservoir and a sample liquid reservoir, whereby a flow rate can be changed while maintaining a narrowed width of a sample flow. There is a problem for this method in that when a concentration of liquid of particles in the disposable flow path cartridge containing sample particle liquid is too high or too low, it is necessary to collect the sample and adjust the concentration of liquid of particles again.

1-3) Technical Problem for Sorting Large Cells or Clump of Cells

In the regenerative medicine, a large scale cell culture is carried out. In this case, cells are not cultured separately from each other, but usually cultured under a condition of a clump of cells (cell spheroid). Thus, a size thereof usually becomes 100 µm or more. While, in a principle of the cell sorter disclosed in Patent literature 1 and Patent literature 15, the object is to flow down liquid droplets into the air from a nozzle and to sort the liquid droplets containing a single cell respectively. Therefore, it is difficult to stably form a droplet containing a clump of cells with a diameter of 100 µm or more. While, Patent literature 21 discloses a technique wherein the diameter of the clump of cells is not limited. In this method, a sideways pulse wind of air is applied to a sequential, stringlike flow from a nozzle to the air, which is not liquid droplets, whereby the unwanted cells are removed to drop and collect the cells of interest. In this method, however, the cells are not sorted in a closed space, and thus the cells are contaminated by bacterium in the air. Further, the whole flow paths are indisposable, and thus this method is not suitable for the aseptic treatment. In the sorting technique for collecting cells in the disposable flow path cartridge described in Patent literature 13, it is examined that the cell spheroid with at least a size of 40 µm can be sorted when a flow path has a cross-section size of a width of 80 µm and a depth of 80 µm. However, it is impossible to flow cell spheroids with a diameter of 100 µm or more in the flow path. Therefore, a technique for aseptically sorting the large clump of cells (cell spheroid) in the disposable cartridge suitable for regenerative medicine, has not been developed yet.

1-4) Problem in Purification of Differentiating Cells in Regenerative Medicine

When a cell sheet and the like consisting of the differentiating cells is transplanted in the regenerative medicine, it is necessary to remove the undifferentiated cells which cause tumors. In the usual differentiation induction, a rate of differentiation induction is not about 100%, that is, at least 1% of the undifferentiated cells are mixed. As the method for removing the mixed undifferentiated cells, there are 1) a general cell sorting method in which the differentiating cells only are sorted using the cell sorter (Patent literatures 1 and 2) and 2) a method for removing the undifferentiated cells using antibody-immobilized magnetic beads described in Patent literature 10. In the general cell sorting method by a liquid droplets separation procedure in the air, there is a problem in that cells are heavily damaged by a bump against the fluid level due to high speed flow during a collection. In the method using the antibody-immobilized magnetic beads, there is a problem in that it is impossible to remove the undifferentiated cells which is not present on the surface of the clump of cells but present in the clump of cells.

1-5) Necessity of Sorting Water-in-Oil Emulsion Droplets in Oil and Problem Thereof Various cells are mixed in a diseased tissue, and therefore it has been recognized that the cells cannot be analyzed by an average data of various cell populations. Under the circumstances, a digital PCR which is insulated from the influence of the contaminating substances by infinitesimally dividing an area of PCR reaction, has been focused on. This method is divided into two main methods, i.e. an emulsion method and a multi-chamber method. The emulsion method has an advantage in analysis of one hundred thousand cells or more, and the multi-chamber method has an advantage in analysis of about ten thousand cells or less. While, a next-generation DNA sequencer which archives ten thousand fold performance and cost-performance improvement in the last ten years, is creating a new marketplace in the future. High sample purification is required in the next-generation DNA sequencer (Non-patent literatures 2 and 3). As a tool for purification, a method for sorting the water-in-oil emulsion droplets after the digital PCR is required. Problems on the sorting of the water-in-oil emulsion droplets are explained below.

In the present invention, a cell is incorporated into a minute reaction area, and then the digital PCR which targets a partial sequence of genes in the cells, is carried out, whereby the water-in-oil emulsion droplets containing the partial sequence of target genes are labeled with specific fluorescence. Then, the particles (droplets) in emulsion containing target genes are sorted using the fluorescence as a marker, and subsequently the entire gene of the single cell included in the particle is amplified. The object of the present invention is to provide a pretreatment apparatus for analyzing the amplified gene by the sequencer in detail and a method thereof. In this method, it is necessary to treat the sample in the disposable chip in order to prevent DNA contaminations. The problems of this method are as follows.

Regarding the digital PCR technique using the water-in-oil emulsion droplets, a method using fluorine oil is described in Patent literature 19. As the fluorine oil, a fluorinert and the like are known. The fluorinert has a high specific gravity, and thus the liquid droplets in fluorine oil float on top of the oil. When the particle in emulsion is sorted in the disposable flow path cartridge, the liquid droplets are floating on the top of the reservoir on the disposable flow path cartridge. Therefore, there is a problem in that when oil flows from the bottom of the reservoir and an upper surface of oil becomes low, about 80% of liquid droplets in the whole emulsion adhere to an inside wall of the reservoir and it has major losses.

1-6) Problem in Flow Rate

A cell sorting apparatus such as a cell sorter is based on the premise that a flow rate can be constantly controlled. This reason is as follows: The particle is detected and identified in liquid, and then if the particle is of interest the particle is sorted at a downstream side of the detecting position. Since a time for reaching from the detecting position to sorting position varies by flow rate, a constant flow rate is required in order to sort the particle at a predetermined time after detection.

The flow rate in the path can be adjusted by an applied pressure. A relationship between the pressure and the flow rate varies by a viscosity of a buffer containing samples and a viscosity of the sheath liquid which flows therewith in order to narrow the sample liquid. Therefore, a type of buffer and the sheath liquid are generally designated by manufacturing in a commercially available cell sorter.

Under the above circumstances, specific mediums are usually used according to cell types in order to measure the living cells. Therefore, in order to adapt to a wide variety of buffers (including mediums) having different viscosities in addition to a specific buffer, a flow rate adjusting technique is required.

2) Problem in a Method for Analyzing a Single Cell

When a differentiating cell population is transplanted in the regenerative medicine, the undifferentiated cells must not include the undifferentiated cells causing tumors. Therefore, it is necessary to detect and remove the undifferentiated cells which are mixed at a low concentration, i.e. about one cell per a million differentiating cells, and thus it is important to control product quality of the differentiating cells. In this regard, an analysis on a single cell and an analysis on a clump of cells are required. For these analyses, as described in Patent literature 1, the digital PCR in which an influence of contaminating cells is removed by using a detecting reaction in a minute area, is suitable. Patent literature 22 discloses an analysing method wherein cells are incorporated in the water-in-oil emulsion droplets one by one and the single cells are analysed using the detecting reaction in the minute area. In connection to this, the PCR reaction is carried out after lysing the cell in emulsion. A detection sensitivity of a conventional PCR is a level capable of detecting a target gene of about a one-thousandth concentration of a non-target gene. On the other hand, there is no influence of the contaminating substances in the digital PCR. Thus, regarding a limit of sensitivity, about a one-millionth target gene can be detected when the reaction area is divided into a million areas. A ratio of cells with a specific gene sequence can be quantified by the above method. On the other hand, in the cells having the specific gene of interest, it is not clear if remaining genes of the cells are identical. Therefore, it is required that the cells having the gene sequence of interest are sorted one by one, and then the whole genome is amplified, and the entire sequence is determined by the next-generation DNA sequencer. In order to perform this method, it is necessary to add a reagent for amplifying the entire genome to the water-in-oil emulsion droplets which are selected by a fluorescence signal after the PCR reaction. As the method, Patent literatures 19 and 22 discloses a method for fusing two different liquid droplets at one-to-one in the flow path.

According to these methods, a whole genome amplifying reaction can be carried out after fusing by adding a reagent for the next reaction to one liquid droplet to be fused. However, the method has a low certainty because positions of each of the droplets cannot be controlled.

While, as a method for analyzing a single cell in detail without using the emulsion, it is considered that the cells are sorted in the disposable flow path cartridge and analyzed by the PCR reaction and the like after a single cell is directly dispensed to a multi-well plate. As such method, a method wherein a dispensed liquid is discharged by a piezoelectric element from a dispensing nozzle is known, as described in Patent literature 17. In this method, there is a problem in that a pressure pulse by the piezoelectric element damages the cells. In the dead cells which are damaged, for example, RNA thereof cannot be analyzed, and therefore a low damage against cells is required in the cell dispensing as well as the cell sorting.

Solution to Problem

Under these circumstances, the present inventors have conducted intensive studies for a method for analyzing a single cell or a cell spheroid, most suitable for regenerative medicine, a method for removing undifferentiated cells from differentiating cells, and apparatuses thereof. As a result, the present inventors surprisingly found that the above problems can be solved by the following apparatuses and methods.

The present invention is based on the above findings.

Therefore, the present invention relates to

[1] an apparatus for analyzing and separating particles comprising:

a flow path cartridge in which a flow path is formed in a transparent substrate, an illumination unit configured to illuminate particles in a sample liquid flowing through the flow path, a detection unit configured to detect particles of interest by detecting scattered light or fluorescence generated from the particles when the particle is illuminated, and identifying the particle based on its signal intensity, a force generating unit configured to apply a force for changing a flow direction to the particles which flow in the flow path of the cartridge based on the signal from the detection unit, wherein a sample liquid reservoir (sample reservoir) connected to a first flow path; a fourth branched flow path and a fifth branched flow path which are oppositely connected to both sides of the first flow path; a third-A reservoir connected to the fourth branched flow path for delivering a pulse flow thereto;

a third-B reservoir connected to the fifth branched flow path for changing a particle course through the pulse flow generated by the force generating unit, which flows from the fourth branched flow path to a direction of the fifth branched flow path, to sort and collect the particles; and a fourth reservoir connected to a downstream side of the first flow path for reserving particles which are not sorting; are formed on the cartridge, and each reservoir is covered by a seal cover so that the inside of the each reservoir is sealed from the outside,

[2] the apparatus for analyzing and separating particles of the item [1], comprising:

a flow path cartridge in which a flow path is formed in a transparent substrate, an illumination unit configured to illuminate particles in a sample liquid flowing through the flow path, a detection unit configured to detect particles of interest by detecting scattered light or fluorescence generated from the particles when the particle is illuminated, and identifying the particle based on its signal intensity, a force generating unit configured to apply a force for changing a flow direction to the particles which flow in the flow path of the cartridge based on the signal from the detection unit, wherein a sample liquid reservoir (sample reservoir) connected to a first flow path; a fourth branched flow path and a fifth branched flow path which are oppositely connected to both sides of the first flow path;

a third-A reservoir connected to the fourth branched flow path for delivering a pulse flow thereto;

a third-B reservoir connected to the fifth branched flow path for changing a particle course through the pulse flow generated by the force generating unit, which flows from the fourth branched flow path to a direction of the fifth branched flow path, to sort and collect the particles; and a fourth reservoir connected to a downstream side of the first flow path for reserving particles which are not sorting; are formed on the cartridge, and each reservoir is covered by a seal cover so that the inside of each reservoir is sealed from the outside, wherein the apparatus comprises a means which equalizes air pressure in each reservoir with the air pressure of an in-device air pressure control system, and a stream of the flow path in the cartridge is controlled by controlling the air pressure in each reservoir through each in-device air pressure control system,

[3] the apparatus for analyzing and separating particles of the item [1], comprising:

a flow path cartridge in which a flow path is formed in a transparent substrate, an illumination unit configured to illuminate particles in a sample liquid flowing through the flow path, a detection unit configured to detect particles of interest by detecting scattered light or fluorescence generated from the particles when the particle is illuminated, and identifying the particle based on its signal intensity, a force generating unit configured to apply a force for changing a flow direction to the particles which flows in the flow path of the cartridge based on the signal from the detection unit, wherein a sample liquid reservoir (sample reservoir) connected to a first flow path; a fourth branched flow path and a fifth branched flow path which are oppositely connected to both sides of the first flow path;

a third-A reservoir connected to the fourth branched flow path for delivering a pulse flow thereto;

a third-B reservoir connected to the fifth branched flow path for changing a particle course through the pulse flow generated by the force generating unit, which flows from the fourth branched flow path to a direction of the fifth branched flow path, to sort and collect the particles; and a fourth reservoir connected to a downstream side of the first flow path for reserving particles which are not sorting; are formed on the cartridge, and each reservoir is covered by a seal cover so that the inside of each reservoir is sealed from the outside, wherein seal covers of the third-A reservoir for delivering a pulse flow and the third-B reservoir for collecting the particles are stretchable and deformable membranes, and the apparatus has actuators which externally apply a mechanical force to the seal covers to displace the seal covers, and a sorting unit configured to sort the particles by generating the pulse flow in the branched flow paths through an action for pushing down the seal cover of the third-A reservoir at high speed, and an action for drawing up the seal cover of the third-B reservoir using the actuators, when the particles pass through a sorting region

[4] an apparatus for analyzing and/or separating particles comprising:

a flow path cartridge equipping a first flow path for introducing a sample liquid containing particles, a second flow path and a third flow path for introducing a sheath liquid, arranged on both sides of the first flow path, a first joining flow path joining the first, second, and third flow paths, a first reservoir for reserving the sample liquid, a second reservoir for reserving the sheath liquid, and a reservoir (fourth reservoir) for reserving a discharged liquid, which are formed on a substrate, an illumination unit configured to illuminate particles flowing through the first joining flow path, a detection and analysis unit configured to detect and analyze scattered light or fluorescence generated from the particles, wherein the flow path cartridge has the first to third flow paths on an upstream side of the first joining flow path, the first flow path is connected to the first reservoir, the second and third flow paths are connected to the second reservoir, the first joining flow path comprises a flow path pattern connected to the fourth reservoir at the downstream side, and the apparatus has a means for controlling a narrowed width of sample flow and a sample flow rate by controlling pressures of the first reservoir, the second reservoir, and the fourth reservoir, respectively,

[5] an apparatus for analyzing and separating particles comprising:

a flow path cartridge in which a flow path is formed in a transparent substrate, an illumination unit configured to illuminate particles in a sample liquid flowing through the flow path, a detection unit configured to detect particles of interest by detecting scattered light or fluorescence generated from the particles when the particle is illuminated, and identifying the particle based on its signal intensity, a force generating unit for changing a flow direction to the particles which flows in the flow path of the cartridge based on the signal from the detection unit, wherein a sample liquid reservoir (sample reservoir) connected to a first flow path; a fourth branched flow path and a fifth branched flow path which are oppositely connected to both sides of the first flow path;

a third-A reservoir connected to the fourth branched flow path for delivering a pulse flow thereto;

a third-B reservoir connected to the fifth branched flow path for changing a particle course through the pulse flow generated by the force generating unit, which flows from the fourth branched flow path to a direction of the fifth branched flow path, to sort and collect the particles; and a fourth reservoir connected to a downstream side of the first flow path for reserving particles which are not sorting; are formed on the cartridge, and each reservoir is covered by a seal cover so that the inside of each reservoir is sealed from the outside, wherein a flow path width and a flow path depth of the flow paths are 150 μm or more, and a size of an illumination laser beam in the direction of flow path width is 100 μm or more,

[6] a method for purifying differentiating cells using the apparatus of any one of the items [1] to [5], characterized in that low-concentrated, undifferentiated cells mixed in the differentiating cells, which are differentiated from the undifferentiated cells, are removed, wherein a force for changing a flow direction is applied to the undifferentiated cells so as to change the course thereof and a force for changing a flow direction is not applied to the differentiating cells so as not to change the course thereof based on the signal from the detection unit, whereby the undifferentiated cells are removed from the differentiating cells contained in the fourth reservoir so as to recover a cell liquid and increase a collection rate of the differentiating cells,

[7] a method for purifying differentiating cells of item [6], wherein the recovered cell liquid is subjected to the same treatment for removing the undifferentiated cells repeatedly,

[8] a device for dispensing particles contained in a sample liquid one by one, wherein a dispensing nozzle is an automatically-disposable, transparent hollow pipette, a dispensed liquid volume is 0.30 μL or less, the dispensed liquid in the hollow pipette is wholly image-recognized per every dispensing, to thereby detect a presence or absence of the particle having a diameter of 10 μm or more, and the number thereof, and the predetermined number of particles are dispensed to a multi-well plate,

[9] an apparatus for analyzing and separating particles comprising:

a flow path cartridge in which a flow path is formed in a transparent substrate, an illumination unit configured to illuminate particles in a sample liquid flowing through the flow path, a detection unit configured to detect particles of interest by detecting scattered light or fluorescence generated from the particles when the particle is illuminated, and identifying the particle based on its signal intensity, a force generating unit configured to apply a force for changing a flow direction to the particles which flows in the flow path of the cartridge based on the signal from the detection unit,
wherein the cartridge has a sample liquid reservoir (sample reservoir) connected to a flow path and a reservoir connected to a flow path for sorting and collecting the particles from the flow path by changing a flow direction through the force generating unit, and an inside wall of the sample reservoir or the reservoir for collecting the sorted particles is covered by a water-shedding material or an adaptor made from a water-shedding material,

[10] an apparatus for analyzing and separating particles of the item [9], wherein the water-shedding material is fluorine resin,

[11] a method for forming liquid droplets in oil by joining oils to a flow path flowing a sample liquid through flow paths which are joined to the flow path from either side thereof, wherein a specific gravity of the liquid droplets is increased compared to that of oil by mixing a component having high specific gravity to the sample liquid,

[12] the method for forming liquid droplets in oil of the item [11], wherein the component having high specific gravity is polytungsten, bromoform, or iodomesylene,

[13] an apparatus for measuring particles or sorting particles comprising:
 a flow path cartridge in which a flow path is formed in a transparent substrate,
 an illumination unit configured to illuminate a part of the flow path in which particles in a sample liquid flow,
 a detection unit configured to detect scattered light or fluorescence generated when each of the particles passes through an illumination region,
 a unit configured to identify a particle of interest based on each light signal,
wherein the apparatus comprises a unit configured to measure a flow rate of each of the particles, and a unit configured to control the flow rate of each of the particles so as to maintain a constant flow rate thereof,

[14] the apparatus for measuring particles or sorting particles of the item [13], wherein the unit configured to measure a flow rate is an illumination optical system in which two illumination lights with different wave lengths are respectively illuminated onto two positions with a certain separation in a flow direction, and the unit configured to control the flow rate is one in which the time change of the pulse shape of scattered light intensity of each of the wave lengths generated when the particle passes through is measured, the flow rate of each particle is measured based on a time lag of peak values of each of the pulse shapes, and the flow rate is controlled so as to maintain a constant mean flow rate thereof

[15] a method for measuring particles or sorting particles using the apparatus of the item [13] or [14], wherein the particles are suspended in any buffer,

[16] a method for measuring particles or sorting particles of the item [15], wherein the buffer is aqueous liquid or oily liquid

[17] a cell gene analysis system comprising:
 a unit for forming in-oil liquid droplets containing cells, a cell lysis reagent, and a reagent for PCR reaction,
 a unit for performing a PCR reaction after a cell lysis reaction,
 a unit for sorting in-oil liquid droplets by a fluorescent staining after the PCR reaction, and
 a unit for dispensing the sorted in-oil liquid droplets one by one,

[18] the cell gene analysis system of the item [17], wherein the cell is a single cell or a single cell spheroid,

[19] the cell gene analysis system of the item [17] or [18], wherein the unit for forming in-oil liquid droplets is a disposable flow path cartridge, a width of flow path flowing cells in the disposable flow path cartridge is at least 100 μm, and a size of the in-oil liquid droplets can be controlled to a range from 40 μm to 100 μm,

[20] the cell gene analysis system according to any one of the items [17] to [19], wherein the dispensing unit is for a multi-well plate, and a liquid to be discharged from a dispensing nozzle is pushed out while being brought into contact with an inside wall of the multi-well plate, or with a liquid in the multi-well plate,

[21] The cell gene analysis system according to any one of the items[17] to [20], wherein the dispensing nozzle in the dispensing unit is automatically-disposable, transparent hollow pipette, a dispensed liquid volume is 0.34, or less, the dispensed liquid in the hollow pipette is wholly image-recognized per every dispensing, the dispense liquid is discharged only when one particle having a diameter of 10 μm or more is present in the dispense liquid,

[22] a gene analysis method comprising the steps of:
 forming in-oil liquid droplets containing cells, a cell lysis reagent, and a reagent for PCR reaction,
 performing a PCR reaction after a cell lysis reaction,
 sorting in-oil liquid droplets by a fluorescent staining after the PCR reaction, and
 dispensing the sorted in-oil liquid droplet one by one,

[23] the gene analysis method of the item [22], wherein the cell is a single cell or a single cell spheroid,

[24] the gene analysis method of the item [22] or [23], wherein a disposable flow path cartridge is used in the step of forming in-oil liquid droplets, a width of flow path flowing cells is at least 110 μm, and a size of the formed in-oil liquid droplets is 40 μm to 100 μm,

[25] the gene analysis method according to any one of the items [22] to [24], wherein the in-oil liquid droplet is dispensed to a multi-well plate in the step of dispensing the in-oil liquid droplet, and a liquid to be discharged from a dispensing nozzle is pushed out while being brought into contact with an inside wall of the multi-well plate, or with a liquid in the multi-well plate,

[26] the gene analysis method according to any one of the items [22] to [25], wherein the dispensing nozzle in the dispensing step is automatically-disposable, transparent hollow pipette, a dispensed liquid volume is 0.34, or less, the dispensed liquid in the hollow pipette is wholly image-recognized per every dispensing, the dispense liquid is discharged only when one particle having a diameter of 10 μm or more is present in the dispense liquid, and

[27] an apparatus for forming water-in-oil emulsion droplets, wherein a flow path for forming in-oil liquid droplets is in a disposable flow path cartridge, plural reservoirs connected to flow paths are formed on the cartridge, a width of flow path flowing cells is at least 110 μm, and a size of the formed in-oil liquid droplets can be controlled to a range from 40 μm to 100 μm by controlling an air pressure above liquids in each of the reservoirs.

Advantageous Effects of Invention

According to the present invention, aseptically sorting in an enclosed space, which is required in the regenerative medicine, can be carried out. Further, the present invention ensures that the undifferentiated cells mixed in the differentiating cells which are inductively-differentiated from iPS cells or ES cells, are efficiently removed; as a result, the number of undifferentiated cells per $10^6$ of differentiating cells is zero. Furthermore, the clump of cells (cell spheroids) with a diameter of 100 μm or more can be sorted, and thus it is possible to remove the undifferentiated cells included in the clump of cells as a cell mass. In addition, it becomes possible to analyze genes per cell or genes per cell spheroid.

BRIEF DESCRIPTION OF THE DRAWINGS

FIG. 5 shows (A) illumination positions of two lasers for measuring the flow rate in the disposable flow path cartridge for sorting, and (B) a signal measurement method for measuring the flow rate.

FIG. 12 shows (A) a measuring example of a flow rate in the case that the flow rate is adjusted by varying the pressure in the sample liquid reservoir of the disposable flow path cartridge, and a measuring example in the case that the width of a sample flow is adjusted by varying the pressure in the sample liquid reservoir of the disposable flow path cartridge.

FIG. 14 is a measuring example of the flow rate distribution of particles.

FIG. 15 is evaluation examples of (A) a removal efficiency of the undifferentiated cells in regenerative medicine (an undifferentiated cell ratio is 20%), and (B) a removal efficiency of the undifferentiated cells in regenerative medicine (an undifferentiated cell ratio is no more than 0.3%).

DESCRIPTION OF EMBODIMENTS

Figure 1:
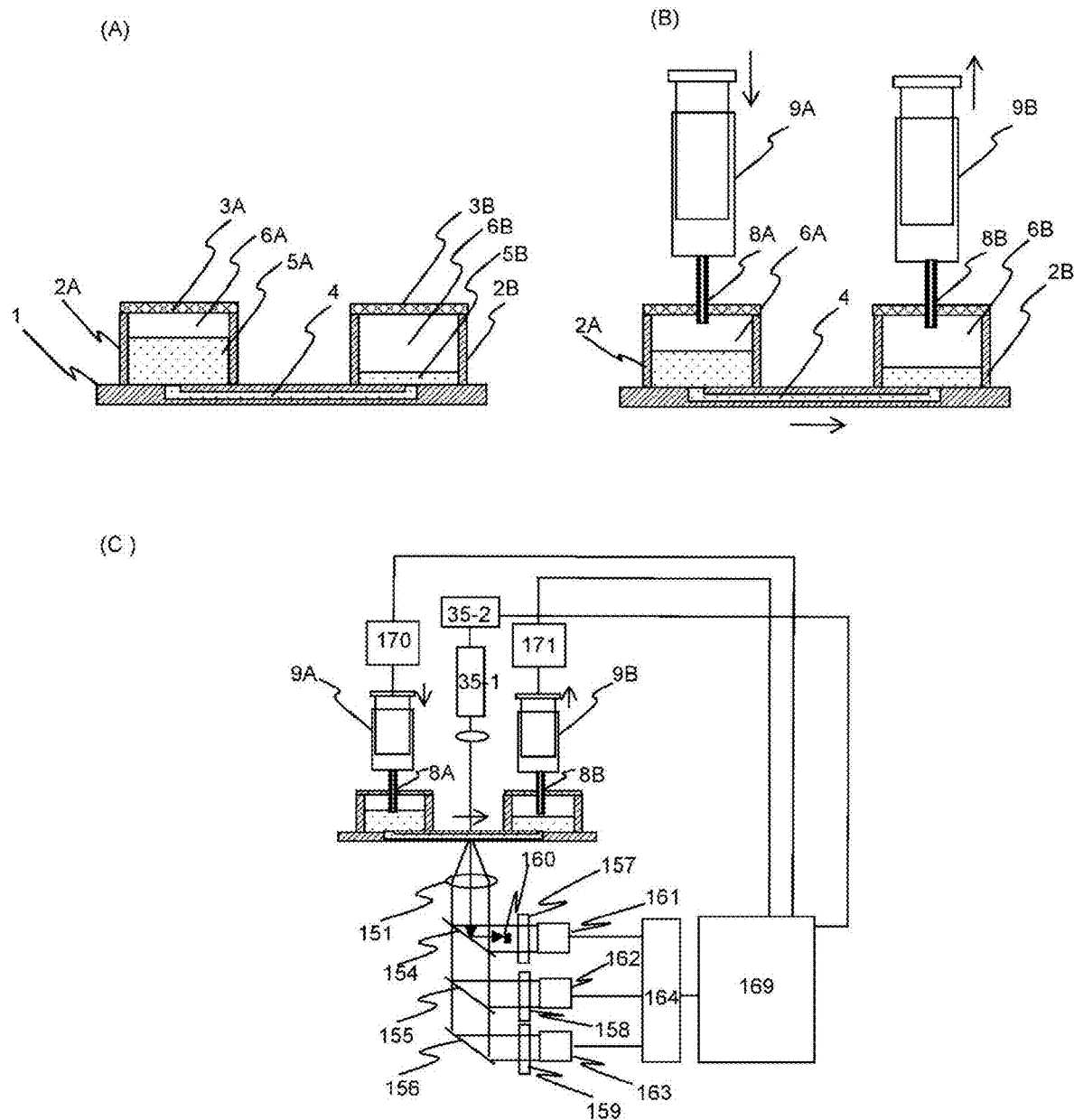
FIG. 1 shows (A) a status of a closed system wherein the reservoir in the disposable flow path cartridge is covered, (B) a method for externally-controlling the liquid flow in the cartridge flow path in the status wherein the reservoir in the disposable flow path cartridge is covered, and (C) a measuring system for analyzing particles in the flow path in the above method (B).

1) Embodiments of Means for Solving Problems in Sorting

When a cell-sorting device is applied in regenerative medicine, a method for sorting cells in a closed system of the disposable flow path cartridge is suitable. Further, for gene analysis of a single cell by the digital PCR, a sorting technique of the water-in-oil emulsion droplets in the disposable flow path cartridge, without DNA contamination between samples, is suitable. However, there are some problems and thus it is required to solve these problems. Embodiments for solving these problems are explained below.

1-1) Embodiment for Solving a Problem in the Sorting for the Aseptic Treatment

The apparatus for analyzing and separating particles of the present invention is characterized in that it comprises a flow path cartridge in which a flow path is formed in a transparent substrate, an illumination unit configured to illuminate particles in a sample liquid flowing through the flow path, a detection unit configured to detect particles of interest by detecting scattered light or fluorescence generated from the particles when the particle is illuminated, and identifying the particle based on its signal intensity, a force generating unit configured to apply a force for changing a flow direction to the particles which flow in the flow path of the cartridge based on the signal from the detection unit, wherein a sample liquid reservoir (sample reservoir) connected to a first flow path; a fourth branched flow path and a fifth branched flow path which are oppositely connected to both sides of the first flow path; a third-A reservoir connected to the fourth branched flow path for delivering a pulse flow thereto; a third-B reservoir connected to the fifth branched flow path for changing a particle course through the pulse flow generated by the force-generating unit, which flows from the fourth branched flow path in the direction of the fifth branched flow path, to sort and collect the particles; and a fourth reservoir connected to a downstream side of the first flow path for reserving particles which are not sorted;

are formed on the cartridge, and each reservoir is covered by a seal cover so that the inside of each reservoir is sealed from the outside.

The apparatus for analyzing and separating particles of the present invention is explained using FIGS. 1(A) and (B). FIG. 1(A) shows a method for controlling a flow of the flow path in the airtight flow path cartridge having two simple reservoirs. The reservoir 2A and the reservoir 2B are formed on the substrate 1 and connected with the flow path 4 formed in the substrate 1. Each of the reservoirs is hermetically capped by the cover 3A and cover 3B, respectively. These covers are made from deformable gum. A material of the cartridge is a transparent resin, and any one material of COP, COC, and PMMA is preferable. As the material of the cover, a teflon-(registered trademark) based elastomer which is a water repellent material and a stretchable resin is preferable, but normal silicon rubber is also preferable. That is, in the apparatus for analyzing and separating particles of the present invention, each of the reservoirs is covered by a seal cover and thus the inside of each reservoir is sealed from the outside, and for example, the cells can be analyzed and sorted aseptically. Further, the feature in that the reservoir is covered by the seal cover, can be applied to the apparatuses of all embodiments described in this specification.

In the flow path cartridge used in the present invention, the reservoir is covered by the seal cover, as mentioned above. In use, a hollow needle-like tube hermetically penetrates through the cover, whereby the air pressure control system in the apparatus is communicated with the inside of the reservoir to become available. The hollow needle-like tube is an example of the means for uniforming an air pressure in the reservoir and an air pressure of an air pressure control system in the apparatus.

For example, FIG. 1(B) shows a state wherein hollow needles 8A and 8B hermetically penetrate through the cover 3A and cover 3B. The hollow needle is preferably made from stainless steel. The hollow needles 8A and 8B are connected to the syringe pumps 9A and 9B, respectively. In this situation, the syringe pump 9A is pushed to apply a positive pressure and the syringe pump 9B is pulled to apply a negative pressure, whereby the sample liquid 5A in the cartridge flows in the flow path 4 and moves to the discharged liquid 4. The hollow needle-like tube hermetically penetrates through the cover of each reservoir and the cartridge is placed on the apparatus, whereby the air pressure of the air pressure control system in the apparatus and the air pressure in the reservoir can become uniformed. That is to say, as one of the means for uniforming the air pressure of the air pressure control system and the air pressure in the reservoir, the multiple hollow needle-like tubes connected to the multiple air pressure control systems in the apparatus hermetically penetrate through the covers of each of the reservoirs and the cartridge is placed on the apparatus, whereby the air pressures can be adjusted. The means for uniforming the air pressures can be applied to the apparatuses of all embodiments described in this specification.

Figure 19:
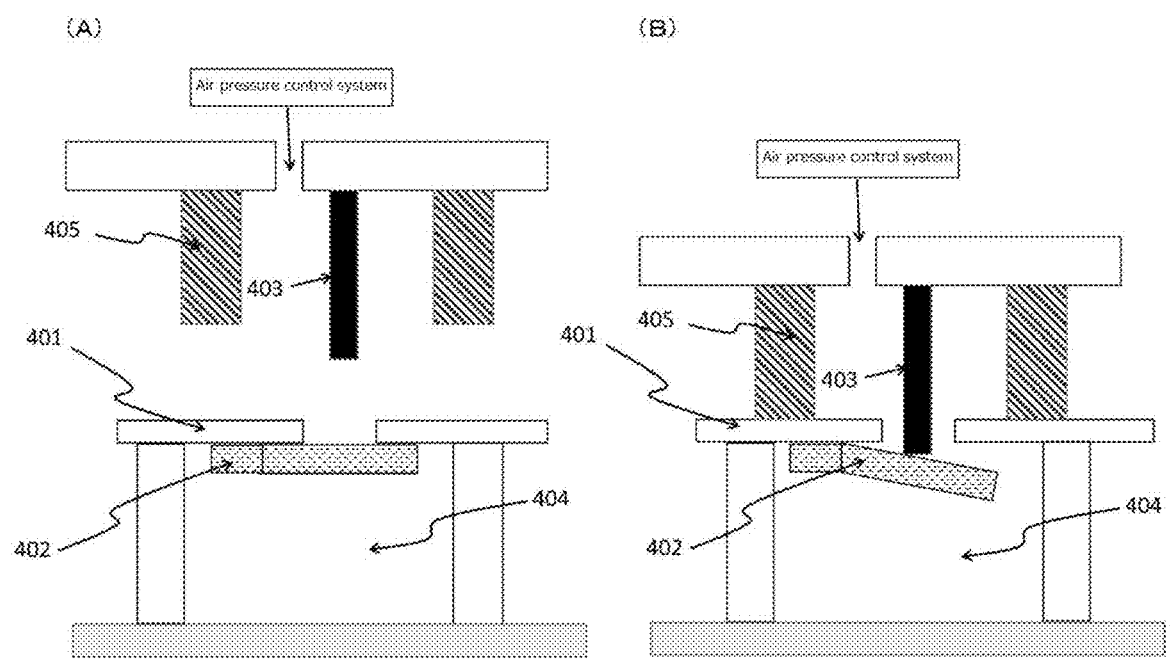
FIG. 19 is a view showing an embodiment of the means for uniforming an air pressure of an air pressure control system and an air pressure in a reservoir.

As the means for uniforming the air pressure of the air pressure control system and the air pressure in the reservoir other than the above means, the structure described in FIG. 19 can be used. The seal cover over the reservoir is a double-layered structure consisting of a hole-opening cover 401 and a cover 402 capable of closing the hole, and an air sealing structure is maintained by contact of the two layers. As shown in FIG. 19 (B), for example, the hole region of the double-layered structure cover is pushed by, for example, a pole 403 from above, whereby one of the double-layered covers is separated from the other thereof and the air sealing breaks. As a result, the air pressure in the reservoir and the air pressure of the upper space of the cover are uniformed. When the air pressure of the air pressure control system and the air pressure in the reservoir are uniformed by such a method, it is important to separate the air pressure control system and the reservoir area from an outside environment, for example, in order to aseptically maintain the reservoir area 404. For this purpose, as shown in FIG. 19B, a side wall made from a deformable material such as gum surrounds the pole, and the side wall is brought into contact with the hole-opening cover 401, whereby the air pressure control system and the reservoir area can be separated from an outside environment. The means for uniforming the air pressures can be applied to the apparatuses of all embodiments described in this specification.

As the air pressure control system in the apparatus herein, there may be mentioned a control system by an atmospheric pressure, or a control system by a pump and a valve. Further, the air pressure controlled by the air pressure control system can be adjusted to a negative pressure, a positive pressure, or an ordinary pressure, if necessary. In addition, the feature in that the hollow needle-like tube hermetically penetrates through the cover of each reservoir and the feature of the air pressure control system in the apparatus, can be applied to the apparatuses of all embodiments described in this specification.

In the present invention, a method wherein pressures of a positive pressure side and a negative pressure side are monitored and then the flow rate is controlled by a difference of pressures, is used.

FIG. 1(C) shows the optical system and the control system for illuminating particles such as cells flowing through the flow path in the above flow path cartridge and detecting a light signal from the particles. The flow path 4 is illuminated with an outgoing laser light from a laser light source 35-1. The instant that the particle passes through the illumination region, a scattered light or fluorescence is generated in pulses. These laser lights are collected by an objective lens 151 to become a parallel light. The multiple wavelength-scattered lights and fluorescences are detected by the optical system on the downstream side of the objective lens. In the detection of the scattered light, the same wavelength as the laser illumination light is selected by a dichroic mirror 154 and a band pass filter 157, and then the scattered light is detected by the detector 161. The transmitted laser light is removed by positioning the shielding plate 160 in front of the detector 161. In the detection of fluorescence, the fluorescences are divided into multiple wavelength regions via dichroic mirrors 155 and 156 and band pass filters 158 and 159 at wavelengths longer than the wavelength of the illumination laser light, and detected by detectors 162 and 163, respectively. The output light signals of the detector are analog signals, and thus they are converted to digital quantity by an AD converter 164. Then, they are transmitted to a control computer 169, and results are recorded and displayed by the control computer. The control computer controls an actuator 170 driving an air pump 9A connected to the upstream reservoir and an actuator 171 driving an air pump 9B connected to the downstream reservoir, and whereby the flow rate of the particles flowing through the flow path 4 is controlled. Further, a light intensity of the illumination laser 35 is controlled by controlling a driver circuitry 35-2 of the laser light source 35-1 using the control computer 169.

Figure 2:
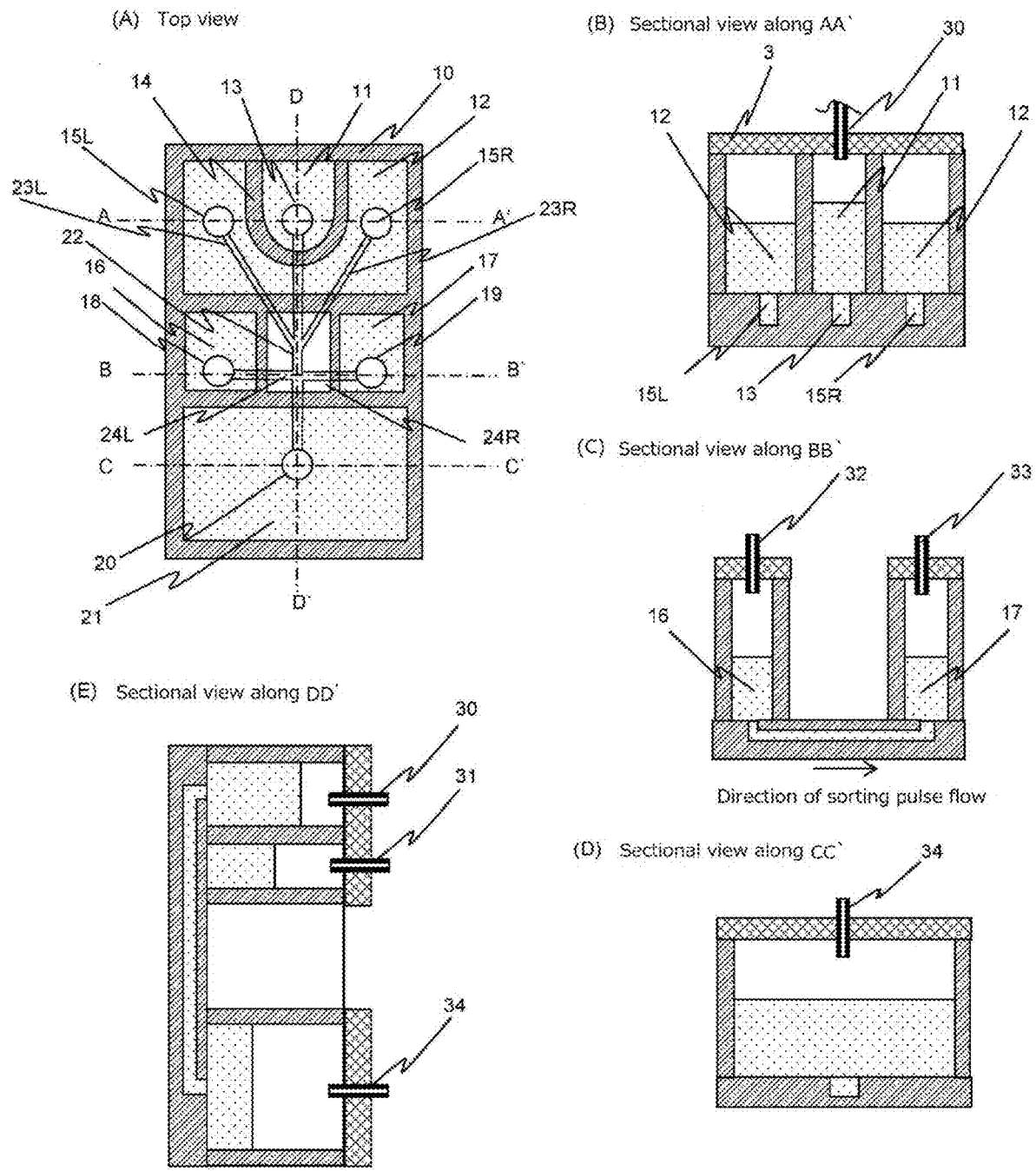
FIG. 2 is (A) a top view of the disposable flow path cartridge for sorting, (B) a cross-sectional view along AA' of the disposable flow path cartridge for sorting, (C) a cross-sectional view along BB' of the disposable flow path cartridge for sorting, (D) a cross-sectional view along CC' of the disposable flow path cartridge for sorting, and (E) a cross-sectional view along DD' of the disposable flow path cartridge for sorting.
Figure 3:
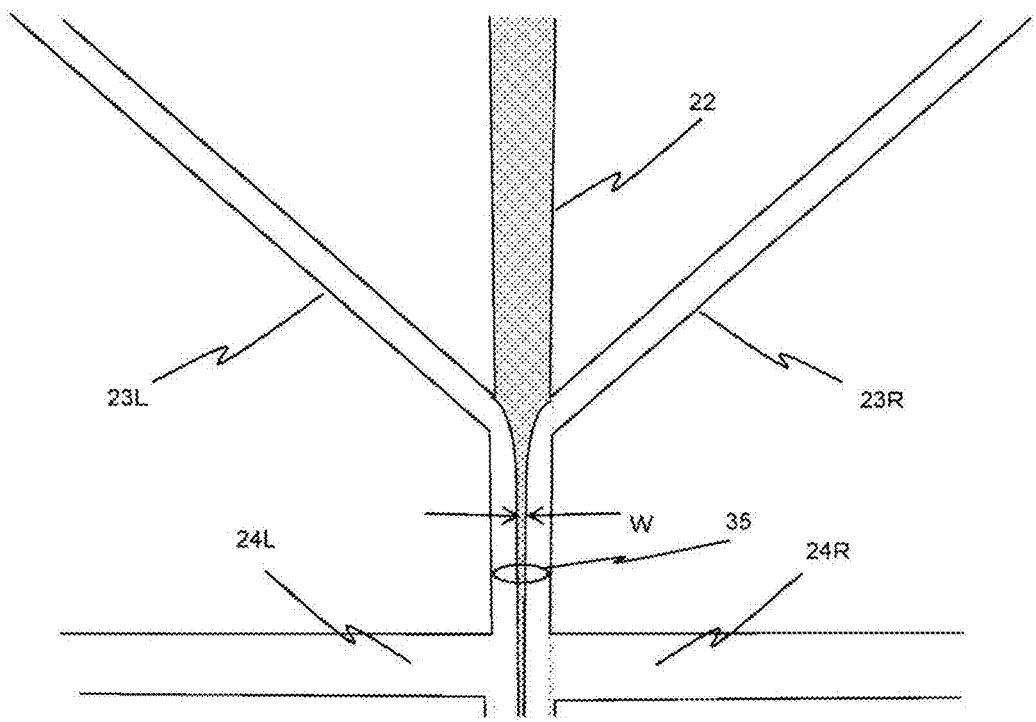
FIG. 3 shows a flow path pattern in the disposable flow path cartridge for sorting.
Figure 10:
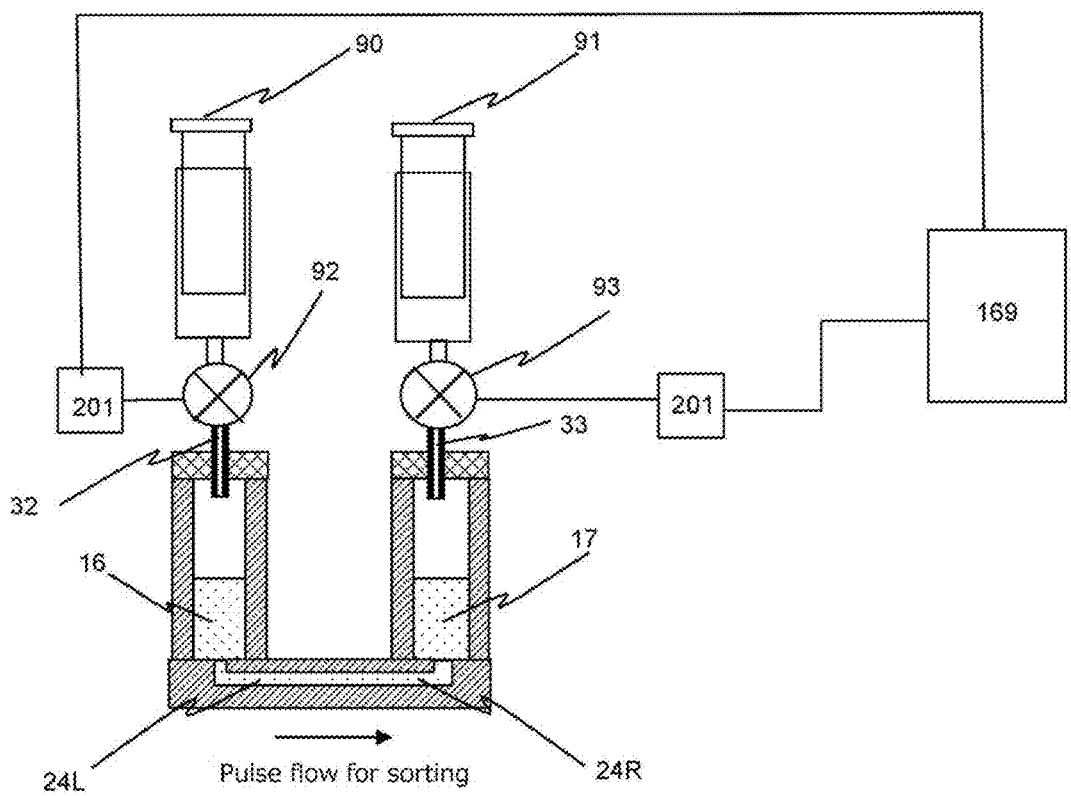
FIG. 10 shows an apparatus, wherein the pulse air pressure through a serial connection of a syringe pump and an electromagnetic valve, is used as a sorting force.

A method for controlling the flow of the liquid in the disposable flow path cartridge for sorting from the outside is explained using FIGS. 2(A), (B), (C), (D), and (E). The object of the air pressure applied to the sample liquid reservoir (sample reservoir: first reservoir) 11, sheath liquid reservoir (second reservoir) 12, and discharged liquid reservoir (reservoir for reserving unsorted particles: fourth reservoir) 21 is to control the flow rate of particles such as cells which flow from an upper stream to a downstream, and therefore a normal constant air pressure may be applied. The "air pressure" applied to the sample liquid reservoir, sheath liquid reservoir, and discharged liquid reservoir is one of the "air pressure control systems" in the present invention. On the other hand, as to the sorting force, a short-lasting pressure pulse must be applied only to specific particles flowing through a main flow path 22. That is, in the present invention, a force-generating unit configured to apply a force for changing a flow direction based on the signal from the detection unit can be used. In FIG. 3, the flow path pattern in FIG. 2 is zoomed in. The target particle for sorting is determined by a signal light from the particle generated in a laser light illumination region 35 (detection region). The instant that the determined target particle passes through the sorting region which is located at the intersection of the main flow path 22 and the sorting flow paths (24L, 24R), a generation of the sorting force is adjusted, whereby the target particle only is sorted. An example of the force-generating unit for generating an air pressure pulse for sorting is shown in FIG. 10. This figure corresponds to a cross-section along BB'. In the method for generating an air pressure pulse, as shown in FIG. 10, a constant air pump and a high speed electromagnetic valve are connected in a series, and then the constant air pump 90 is set at positive pressure and the constant air pump 91 is set at negative pressure (In the present specification, the pressure is based on the atmospheric pressure and described by a differential pressure value from the atmospheric pressure). Then, the air pressure pulses are applied to the insides of reservoirs 16 and 17 by opening valves 92 and 93 for a short time only, whereby the pulse flow for sorting is generated. In connection to this, the above "constant air pump and high speed electromagnetic valve" is also one of the "air pressure control systems." Further, the "constant air pump and high speed electromagnetic valve" is one of the "force-generating units" for applying a pressure pulse for sorting.

Figure 11:
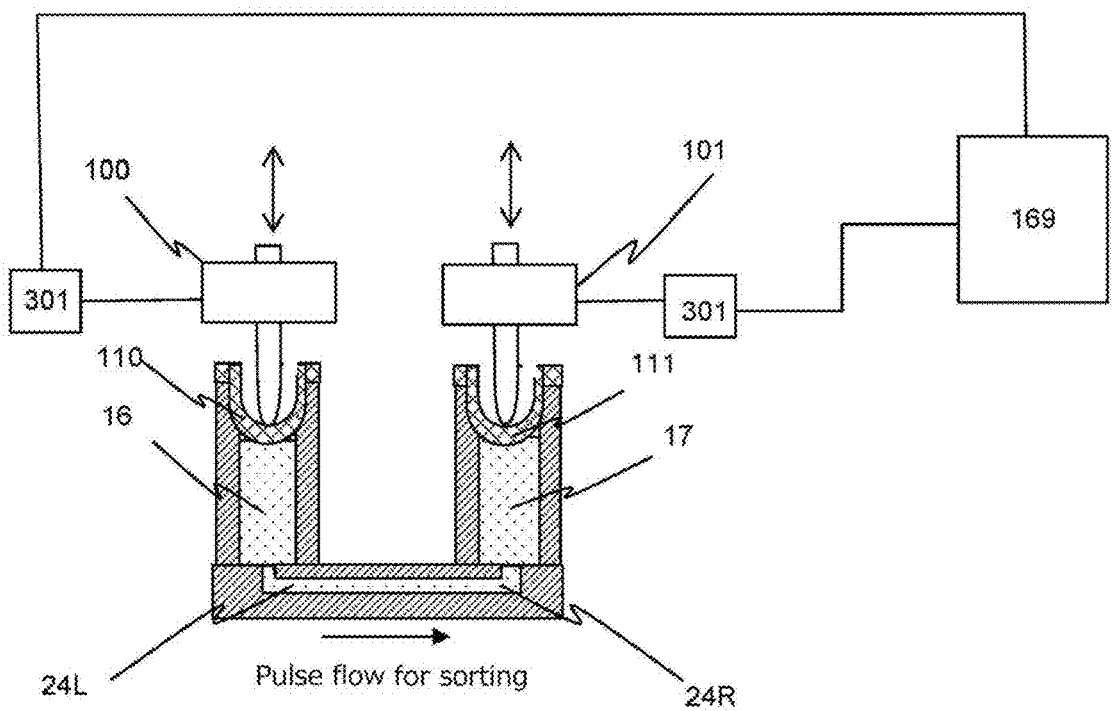
FIG. 11 shows an apparatus wherein forces pushing elastic covers are changed by electromagnetic actuators, and the forces are used as the sorting force.

Next, FIG. 11 shows an example of the "force-generating unit" capable of generating an air pressure pulse which is different from the one described in FIG. 10. In this method, the reservoirs 16 and 17 are sealed by covering thereon using an elastic and stretchable membrane. The membranes 110 and 111 are fixed to the electromagnetic actuators 100 and 101 which are placed on the apparatus, respectively. The instant that the particle determined as a particle to be sorted passes through the sorting region, the electromagnetic actuators 100 and 101 are displaced for a short time only. In this time, a force of the electromagnetic actuator 100 is applied in a direction to push a membrane down, and a force of the electromagnetic actuator 101 is applied in a direction pulling up the membrane. Accordingly, when the electromagnetic actuators are moved in pulses, the sorting flow is generated in pulses. That is to say, the sorting flow can be generated by an action for pushing down the seal cover membrane of the third-A reservoir, and an action for drawing up the seal cover membrane of the third-B reservoir at high speed using the actuators. The particle sorted by the pulse flow for sorting is incorporated into the collection reservoir 17 after a completion of the move of the electromagnetic actuator. It is important not to generate a back-flow which flows the particle back when the pulse flow stops. The back-flow can be protected by cumulatively increasing displacements of the actuator according to the increase of number of sorting. It is preferable that there is no air in the reservoir 16 and 17. When the air is not present therein, there is no process of a compression and an expansion of the air, and thus a time of the response speed of the pressure applied to a liquid in the reservoir quickens. In connection to this, even when the "electromagnetic actuators" to the 3A reservoir and 3B reservoir are used as the force-generating unit for sorting, the normal air pressure and the like by the "air pressure control system" is applied to the sample liquid reservoir, sheath liquid reservoir, and discharged liquid reservoir, and used.

Figure 18:
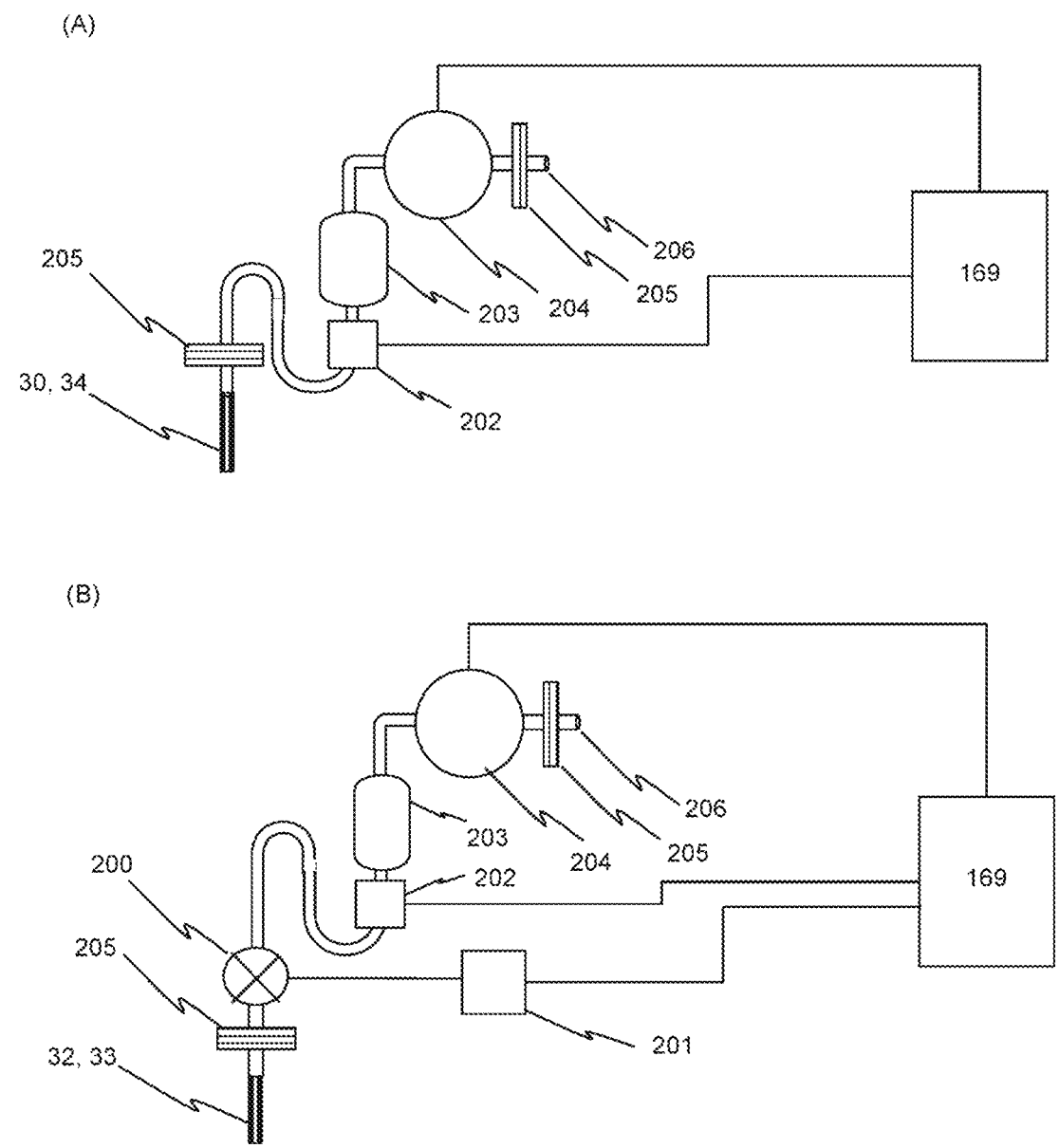
FIG. 18 is (A) a view showing a pressure control using a constant-pressure pump for maintaining a constant flow rate in the constant flow of a sample liquid reservoir, sheath liquid reservoirs, and a discharged liquid reservoir in FIG. 2, and (B) a view showing a system wherein a compressor or a vacuum pump, an electropneumatic regulator, a buffer tank, and an electromagnetic valve are connected, for a pressure control of a sorting liquid reservoir 16 and a collection reservoir 17.

For example, the object of pressure control of the sample liquid reservoir, sheath liquid reservoir, discharged liquid reservoir in FIG. 2 is to maintain a constant flow rate in the constant flow, and thus the control by the constant-pressure pump is used. The control by the constant-pressure pump includes a syringe pump as shown in FIG. 1. As an example other than that above, there may be mentioned a method using a compressor 204 and an electropneumatic regulator 202, as shown in FIG. 18 (A). In the case of the syringe pump, a pressure fluctuation can be disregarded. However, in the electropneumatic regulator, there is constant pressure fluctuation. In order to decrease the pressure fluctuation, a buffer tank 203 is connected thereto. In this way, a constant pressure of 0.1 kPa or less can be controlled with an accuracy of plus or minus 0.025 kPa. In the flow path with a cross-section size of a width of 80 μm and a depth of 80 μm, the constant pressure of the usual range of 0.1 kPa to 30 kPa is used for controlling the constant flow, in order to flow the liquid. Therefore, the accuracy of plus or minus 0.025 kPa in pressure regulation is sufficient capacity.

FIG. 18 (B) shows a system wherein a compressor or a vacuum pump, an electropneumatic regulator, a buffer tank, and an electromagnetic valve are connected, for pressure control of a sorting liquid reservoir 16 and a collection reservoir 17 in FIG. 2. In the pressure control system for the sorting liquid reservoir 16, the pressure of the compressor is set at around 100 kPa, and the control pressure of the electropneumatic regulator is set at around 50 kPa. While, in the pressure control system for the collection reservoir 17, the vacuum pump is set at around −100 kPa, and the control pressure of the electropneumatic regulator is set at around −50 kPa, whereby a sufficient pulse flow as the sorting force is generated, and thus the particles can be sorted.

1-2) Embodiment of Means for Solving a Problem in Adjustment of Sample Concentration A method for adjusting the sample concentration in the disposable flow path cartridge for sorting is explained using FIG. 2. FIG. 2(A) shows a top view of a disposable flow path cartridge for sorting. The flow path cartridge has the sample liquid reservoir (sample reservoir: first reservoir) 11 containing particles such as cells, sheath liquid reservoir (second reservoir) 12, discharged liquid reservoir (reservoir for reserving unsorted particles: fourth reservoir) 21, reservoir for reserving a liquid for sorting pulse flow (3A reservoir) 16, and reservoir for collecting particles (3B reservoir) 17. Each reservoir is connected to the flow path through a port region of the bottom of each reservoir. The sample liquid leads to the flow path 22 through the port 13 of the bottom of the reservoir 11. The sheath liquid leads to the flow path 23L through the left port 15L of the bottom of the reservoir 12, and to the flow path 23R through the right port 15R thereof. When the air pressure is applied to the upper space of the liquid of the reservoir 11 and reservoir 12, the sample liquid is focused to the center of the flow path by joining up with the sheath liquid and flows, as shown in FIG. 3.

Regarding a width of the sample liquid, if the inside pressure of the sample liquid reservoir 11 is made higher than the inside pressure of the sheath liquid reservoir 12, the flow width W of the sample liquid after the joining increases. Conversely, if the pressure of reservoir 11 is made lower than the pressure of reservoir 12, the flow width W decreases. That is to say, it is possible to adjust the width of the sample liquid according to the ratio of the pressures applied to the reservoir 11 and the reservoir 12. Regarding the flow rate of the sample liquid, the flow rate can change while keeping the ratio of the pressures applied to reservoir 11 and reservoir 12, that is, the flow rate can change while keeping the flow width constant by changing the applied pressure. If the concentration of particles or cells to be measured in the sample liquid is high, the width W may be adjusted to reduce while keeping the flow rate constant, and if the concentration of particles or cells to be measured in the sample liquid is low, the width W may be adjusted to increase while keeping the flow rate constant. This adjustment can be carried out by the control of the applied pressure to the reservoir 11 and reservoir 12.

FIGS. 12 (A) and (B) show the relative change of the flow rate and the width of the sample flow in the case that the air pressure in the sheath liquid reservoir is set to 1.8 kPa (based on atmospheric pressure), the air pressure in the discharged liquid reservoir is set to −0.7 kPa (based on atmospheric pressure), and the air pressure in the sample liquid is varied, using the chip of FIG. 2(A). FIG. 12 shows (A) a measuring example in the case of the buffer of the sample liquid being a viscous liquid having a viscosity of 3.6 CP and the sheath liquid being a liquid having a viscosity of 1.07 CP. It can be seen that the width of the flow path is expanded to about 2.6 times with the flow rate remaining substantially constant, when the air pressure of the sample liquid reservoir is increased to about twice the air pressure of 1.8 kPa of the sheath liquid reservoir. On the contrary, when the air pressure of the sample liquid reservoir is set to a lower pressure than 1.8 kPa of the air pressure of the sheath liquid reservoir, it can be seen that the width of the flow path is narrowed with the flow rate increasing. Therefore, it is understood that the flow rate and the width of the flow path may be adjusted according to the following procedure. Firstly, the width of the sample flow is adjusted to the predetermined one by the ratio of the pressure of the sample liquid reservoir and the pressure of the sheath liquid reservoir. Next, the flow rate is only adjusted by controlling the pressure of the discharged liquid reservoir while constantly maintaining the width of the sample flow. In order to adjust the flow rate only without changing the width of the sample flow, the pressure control of the discharged liquid reservoir is important. Further, the flow rate evaluation is required for the adjustment. The flow rate evaluation is described below.

In order to aseptically apply the air pressure to each reservoir, the force-generating unit described in item 1-1) may be applied. Each of the cross-sectional views of FIG. 2 (A) is shown in FIGS. 2(B), (C), (D), and (E). Each reservoir is hermetically covered with a cover 3. In order to apply pressure to the air in an upper space of the sample liquid in the reservoir 11, the hollow needle 30 penetrates through the cover of the reservoir 11 as shown in FIG. 2 (B) and (E). The air inside this needle is connected to the air pressure control system of the apparatus, which is adjusted to the pressure of the reservoir 11 in the apparatus side. In order to apply pressure to the air in the upper space of the sheath liquid in the reservoir 12, the hollow needle 31 penetrates through the cover of the reservoir 12 as shown in FIG. 2 (E). The air inside this needle is connected to the air pressure control system adjusted to the pressure of the reservoir 12 in the apparatus side. The hollow needle 34 penetrates through the cover in the discharged liquid reservoir 21 on the downstream side. The air inside this needle is connected to the air pressure control system adjusted to the pressure of the reservoir 21 in the apparatus side. The pressure applied to the reservoir 21 needs to be equal to or lower than the atmospheric pressure, i.e. a negative pressure. Next, the air pressure control in the reservoir 16 and the reservoir 17 is a control of the pulse pressure for sorting the particles in the sample liquid, which is different from the flow rate control by the air pressure of the constant pressure. As shown in FIG. 10, the method of sorting particles by the pulse pressure is a system in which a constant pressure pump and a normally closed electromagnetic valve are connected in series, and the pulse pressure generated by opening the electromagnetic valve in a short-time is used. It is discriminated as to whether or not the particle is a target particle by the signal light such as scattered light or fluorescence generated when passing through the detection region 35, which is the laser irradiation region. If it is determined that it is the target particle, a positive pressure air pulse is applied to an inside of the reservoir 16 and a negative pressure air pulse is applied to an inside of the reservoir 17, at the timing of passing through a region where the flow path 24L and the flow path 24R cross each other on the downstream side, so that a push flow is generated from the flow path 24L and a pull flow is generated from the flow path 24R. As shown in FIG. 2(C), the hollow needles 32 and 33 penetrate through the reservoir 16 and the reservoir 17 sealed with the cover, respectively.

When an inner diameter of the hollow needle is thin, the response of the air pressure becomes poor, and thus, above a certain inner diameter, is required. If the inner diameter is 1 mm or more, the pressure necessary for sorting particles can be transmitted to the liquid in the flow path via the air in the reservoir even on a short valve opening time, i.e. about milliseconds level.

1-3) Embodiment of Means for Solving a Technical Problem for Sorting Large Cells or Clump of Cells (Cell Spheroid)

In order to sort a clump of cells of 100 μm or more, it is necessary to solve the following problems: It is known that a gravity sedimentation rate becomes faster as the size of the cell or the clump of cells is larger. Thus, the gravity sedimentation rate of the clumps of cells with a large size is fast, and therefore they are deposited in a short period on the port portion at the bottom of the reservoir. Then, when a height of the cell deposit becomes equal to or higher than the depth of the flow path, the flow path is blocked. Therefore, it is necessary to prevent gravity sedimentation for sorting of the clump of cells. The gravity sedimentation of cells can be prevented by mixing components with high specific gravity into a cell suspension buffer and increasing the specific gravity of the buffer. As the components with high specific gravity, polyvinyl pyrrolidone or gellan gum may be used. A cell culture can be carried out after mixing these components into the medium, and damage to the cells can be ignored. The specific gravity of the buffer is not required to be equal to or higher than the specific gravity of the cells, but it is possible to prevent clogging of the cells by slowing down the gravity sedimentation rate. According to our experiments, it is possible to prevent a general spontaneous sedimentation of cells by setting the specific gravity of the buffer to 1.01 or more.

Next, the size of the flow path cross section of the disposable exchange type flow path cartridge will be explained. In order to allow a clump of cells of a size of 100

μm to flow stably without blocking the flow path, a flow path width of 150 μm or more and a flow path depth of 150 μm or more are required. Further, it was found that the size of a clump of cells which can flow without clogging is 40 μm. Therefore, a flow path with a cross section that is at least 40 μm or larger than the maximum size of the clump of cells to be flowed is necessary Further, as a technical problem for sorting large cells or a clump of cells, shortage of the sorting forces may be considered. In order to increase the sorting force, as shown in FIG. 11, it is preferable to apply the force generated by the actuators 100 and 101, which may generate the electromagnetic force directly without interposition of the air, to the liquid flowing as the sorting pulse flow. In this case, the temporal response becomes faster and the force also increases, so it is suitable for sorting large cells and clumps of cells.

1-4) Embodiment of Means for Solving a Technical Problem on Purification of Differentiating Cells in Regenerative Medicine It is examined that a cell sheet or the like consisting of the differentiating cells which are differentiated from iPS cells or ES cells is transplanted in the regenerative medicine. In this case, it is a problem that slightly mixed, undifferentiated cells cause tumors. The rate of differentiation induction is not about 100%, that is, at least 1% of undifferentiated cells are mixed in many cases. A method for aseptically removing undifferentiated cells without cell damage and efficiently purifying differentiated cells will be described below.

For example, it is examined that a process of removing undifferentiated cells contaminating a concentration of 1% in a differentiated cell population is applied to the differentiated cell population. As a method for fluorescently labeling undifferentiated cells specifically, there may be mentioned a method of using a fluorescently-labelled antibody of a surface marker of an undifferentiated cell or a compound that emits fluorescence specifically incorporated into undifferentiated cells described in Non-Patent literature 4. The undifferentiated cells can be stained by the fluorescently-labelled antibody, in a state of disaggregated cells. In contrast, it has been found that the fluorescent compound specifically incorporated into undifferentiated cells can specifically stain undifferentiated cells in tissues. Thus, the undifferentiated cells in the clump of cells can be specifically stained.

It is examined that the following means for sorting cells is applied to a sample of a suspension liquid of a cell population which are specifically fluorescently stained.

The method for sorting the differentiating cells is applied in the flow path cartridge wherein a flow path cartridge in which a flow path is formed in a transparent substrate, an illumination unit configured to illuminate particles in a sample liquid flowing through the flow path, an identification unit configured to identify undifferentiated cells of interest by detecting fluorescence generated from the undifferentiated cells when the undifferentiated cells are illuminated, and identifying the undifferentiated cells based on its signal intensity, a force-generating unit configured to apply a force for changing a flow direction to the undifferentiated cells which flows in the flow path of the cartridge based on the signal from the detection unit, a reservoir which connects to a flow path wherein the undifferentiated cells flow thereinto by charging a direction of flow due to a result of an acting force of the force-generating unit, and a reservoir which connects to a flow path wherein the differentiating cells flow thereinto when a direction of flow is not changed based on the signal from the detection unit. In this case, since the number of differentiating cells per unit time passing through the detection region is 99 times that of the undifferentiated cells. Therefore, when the undifferentiated cells are removed at a treatment rate of 300 cells/second, the collection rate of the differentiated cells is 99 times that, i.e. about 30000 cells/second. Generally, if the mixing ratio of undifferentiated cells is A %, the collection efficiency of differentiated cells may be equivalent to (100−A) times the sorting speed of the device. As the value of A is lower, there are many advantages in improving a processing capacity. Such a method for sorting has been referred to as a negative sorting. FIG. 15 (A) shows the measurement result of the treatment efficiency and the simulation outcome when the total cell number is $2\times10^6$ and the undifferentiating cell ratio is 20%. The result is obtained by performing at a sorting treatment speed of 100 cells/second. As the undifferentiating cell ratio is high, it is consistent with both the actual measurement and the simulation that the undifferentiated cells can be completely removed by the removing treatment of four times. The total required time is 150 minutes, and the efficiency is poor as the undifferentiated cell ratio is as high as 20%. On the other hand, FIG. 15 (B) shows a simulation result when the total number of cells is $10^7$ and the undifferentiated cell ratio is 0.3% or less. The undifferentiated cells are completely removed by the twice removing treatment, and the removing treatment completed within a short time, i.e. within 20 minutes. The higher the ratio of undifferentiated cells, the higher the efficiency.

1-5) Embodiment of Means for Solving a Problem of Sorting in Emulsion

The emulsion will be described on the assumption that the droplets are in oil. If the droplets in emulsion adhere to an inside wall of the reservoir on the disposable flow path cartridge, it causes clogging of the flow path. In order to prevent the adhesion to the inside wall of the reservoir, two methods, i.e. a method of making the inside wall of the reservoir water-shedding and a method of letting it sediment naturally by its own weight even if droplets adhere, will be described below.

Figure 4:
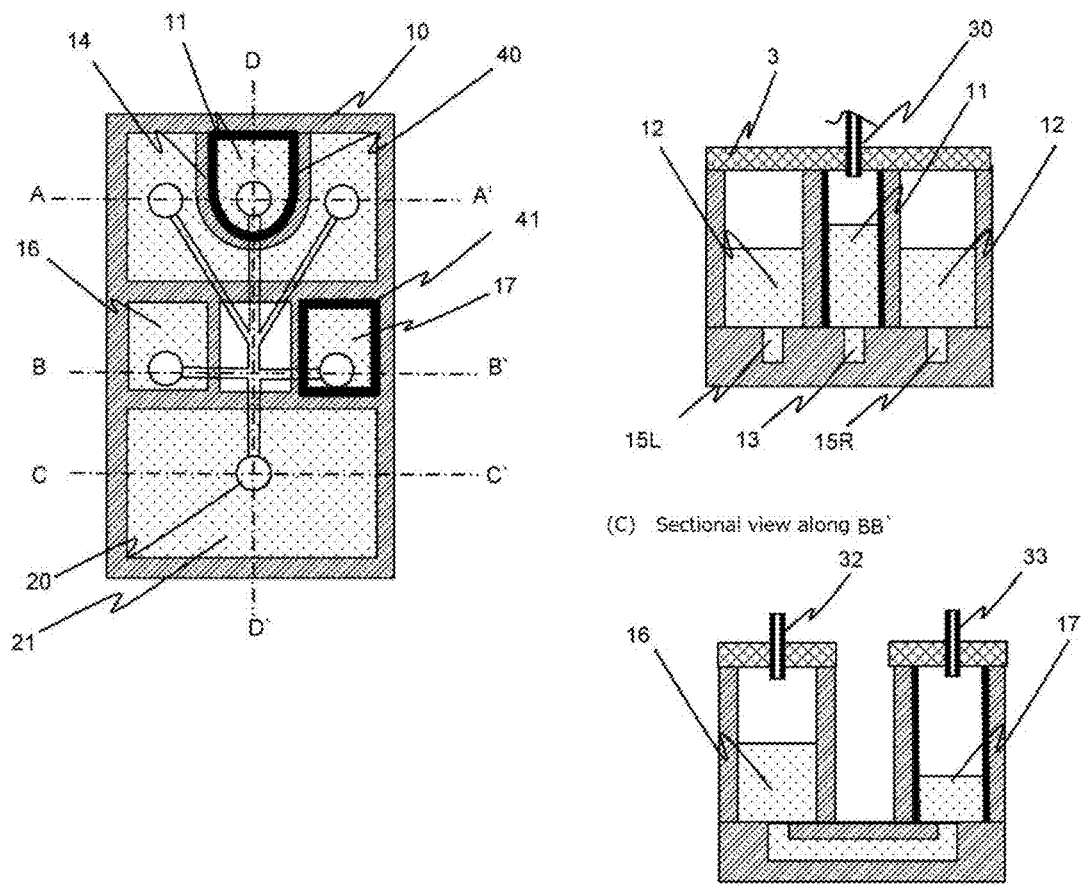
FIG. 4 is (A) a top view of the structure of the disposable flow path cartridge for sorting in the case that the disposable flow path cartridge for sorting of FIG. 2 is used for sorting water-in-oil emulsion droplets, and (B) a cross-sectional view along AA'.

Explanation of Means for Preventing Adhesion by Making the Inside Wall of the Reservoir Water-Shedding FIG. 4 (A) shows the same disposable flow path cartridge as in FIG. 2 (A). It is a problem that the droplets are adhered to the inside wall of the sample liquid reservoir (sample reservoir: first reservoir) 11 containing the particles to be sorted, and the inside wall of the reservoir (third reservoir) 17 wherein the sorted droplets in the emulsion are collected in the cartridge. In order to prevent this problem, a structure in which each of the reservoir 11 and the reservoir 17 is covered with a water-shedding material is shown in FIGS. 4 (A) and 4 (B). Here, the hollow Teflon (registered trademark) adapter is inserted in the reservoir so that the emulsion does not contact the inside wall of the reservoir. The flow path cartridge made by a mold injection using transparent resin, and thus the entire flow path, cannot be made from Teflon (registered trademark). Therefore, it is better to take the above procedure. In addition, it is also possible to coat the inside wall of each of the reservoir 11 and the reservoir 17 with a water-shedding material. Further, a structure covered with a fluoro resin is preferable as the water-shedding coating Embodiment of means for preventing adhesion by increasing a specific gravity of water-in-oil emulsion droplets.

As fluorine oil such as Fluorinert has a heavier specific gravity than that of the liquid droplets, the liquid droplets float in oil. This is because the density of Fluorinert is about 1.8 g/cm$^3$, which is about 1.8 times of water, and thus the liquid droplets float. The specific gravity can be increased by mixing liquid having a specific gravity of 1 or more. Such liquids include sodium polytungstate solution, bromoform solution, or iodomesilene solution. If the specific gravity is about 1.8 g/cm$^3$ or more, the liquid droplets can be settled in the fluorine oil. The saturated aqueous solution of sodium polytungstate has a density of 3.1 g/cm$^3$, the saturated aqueous solution of bromoform has a density of 2.89 g/cm$^3$, and the saturated aqueous solution of iodomesylene has a density of 3.31 g/cm$^3$. In order not to float these components in Fluorinert, it is only necessary to set the density to 1.8 g/cm$^3$ or more. In order to prevent the droplets in the emulsion from adhering to the inner wall of the reservoir, it is not necessary that the density is 1.8 g/cm$^3$ or more. The oil surface moves downward due to oil reduction and the liquid droplets adhering to the inner wall have no buoyancy from the oil. At this time, the density may be high enough to fall downward due to gravity thereof. The density may be in the range of 1.2 g/cm$^3$ to 1.8 g/cm$^3$.

1-6) Embodiment of Means for Solving the Problem on Flow Rate

In a device for sorting cells such as a cell sorter, it is premised that the flow rate can be controlled constantly. The reason for this is as follows. The particles are detected in a liquid, and identified and judged. If it is a target particle, the particle is sorted on the downstream side of the detection position. The time to reach the sorting position from the detection position varies with the flow rate. Thus, it is necessary to maintain the flow rate constantly, in order to sort the particles at a certain time after detection.

The flow rate in the flow path can be adjusted by the applied pressure. However, the relationship between pressure and the flow rate varies depending on the viscosity of the buffer in which the sample is suspended and the viscosity of the sheath liquid flowed together to narrow down the sample liquid. Therefore, types of buffers and sheath liquids are generally limited by manufacturers with commercially available cell sorters.

In the above situation, depending on the type of cell, it is often necessary to use a specific medium in order to measure in a living state. Therefore, a method for adjusting the flow rate is necessary to deal with various buffers, including not only specific buffers but also medium, etc.

Therefore, in cell sorting without cell damage that is desired in regenerative medicine, the flow rate varies depending on various buffers, and thus the function of evaluating the flow rate becomes important. The following measures are adopted to evaluate the flow rate.

In the method for carrying out cell sorting in the disposable flow path cartridge, laser lights of two different wavelengths are emitted to different positions along the flow of the flow path 22 through which the particles flow, as shown in 35 and 36 of FIG. 5 (A). When the particle passes through the two illumination regions, two optical signals (35-A and 36-A) derived from two laser illuminations are generated for each particle as shown in FIG. 5 (B). In the detection of this optical signal, a measurement starts at the moment when the signal 35-A is detected as a signal equal to or larger than the threshold (TH) value set as the detection condition. In this case, the AD conversion of the 35-A signal and the AD conversion of the 36-A signal start at the same time, and the time difference of the times when the optical signals maximize, is recorded. This time difference is a value obtained by dividing the distance (ΔL) between the two illumination positions by the flow rate V of particles. That is, the rates V of each particle can be measured by measuring the time difference ΔT for each particle.

The performance of the AD conversion of the optical signal is as follows. When the sampling frequency is 5 MHz, the signal of the analog time waveform is digitized every 0.2 microseconds so that the time difference of the two signals can be evaluated with a resolution of 0.2 microseconds. In the case where the interval ΔL between the illumination positions of the two lasers is 100 μm and the flow rate V is 1 m/sec, the time difference is 100 μsec, and thus the resolution of 0.2 μsec is sufficient.

The rate evaluation can be carried out for individual particles. For example, in the case of particles generating fluorescence, one of the signals may be scattered light and the other may be fluorescent. In the case of particles which do not generate fluorescence, two scattered light signals may be detected as optical signals. In this case, an optical system is necessary to detect two types of scattered light. As an optical system of detecting each of the scattered lights of two types of lasers suitable for use in a disposable flow path cartridge, the optical system for detecting sideward scattered lights by total reflection at the end face of the flow path substrate described in Patent literature 12 is suitable. In this case, the reflecting surfaces on both sides of the substrate may be used as the optical system for detecting sideward scattered lights derived from two laser wavelengths.

As described above, when the flow rate of each particle is determined, the time difference from the time of the detection region to the time of the cell sorting region is calculated. At the timing of passing through the cell sorting region, it is possible to sort cells by applying a sorting force to the cells.

Further, the flow rate varies by changing the type of buffer in which the particles are suspended, or changing the viscosity of the buffer due to temperature. At this time, the air pressure is adjusted so that the average flow rate of particles is constant. In this case, a pressure condition of each reservoir is preliminarily initialized by the used buffer so that the desired flow path width and the flow rate are set, and the analysis and collection of particles are started under the condition. The flow rate frequently varies depending on ambient temperature, even with initial setting conditions. Therefore, the flow rate of each particle is monitored, and the pressure of the discharged liquid reservoir is controlled via a control PC so that the average value of the flow rate per certain number of particles becomes the desired value.

Figure 13:
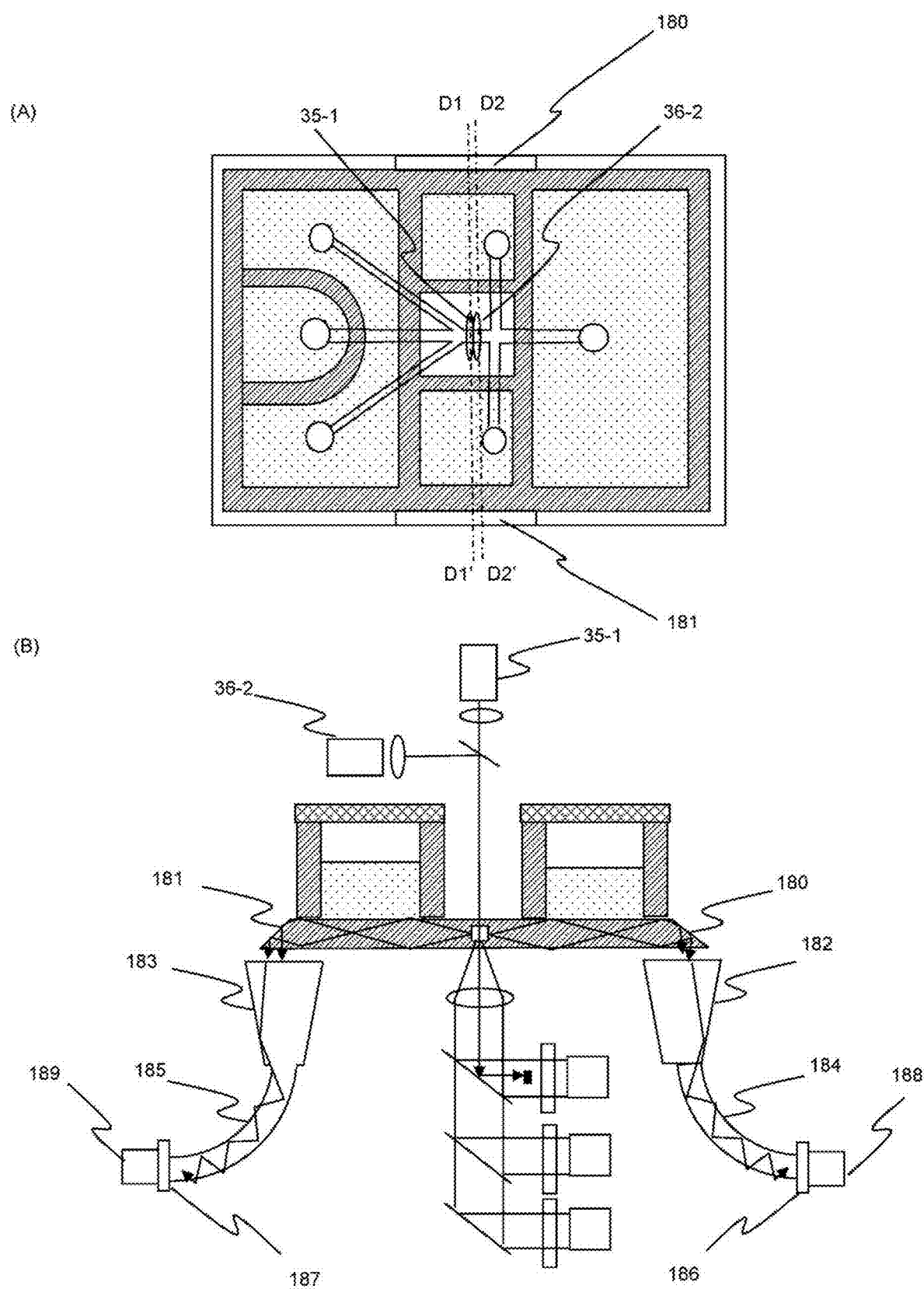
FIG. 13 is examples of (A) the disposable flow path cartridge structure wherein the flow rate was measured by sideward scattering signals of two wavelength lasers, and (B) the optical system of a device wherein the flow rate was measured by sideward scattering signals of two wavelength lasers.

FIG. 13 (A) shows the same disposable flow path cartridge as in FIG. 2 (A). A measurement system for evaluating the flow rate of cells is illustrated, when both ends of a transparent flow path substrate are reflecting surfaces (180 and 181) and a plurality of lasers with different wavelengths are mounted. The reflecting surfaces (180 and 181) are inclined surfaces at an angle of 45 degrees in the vertical direction, and the surface thereof is mirror-finished. FIG. 13 (B) shows both of the D 1 D 1 'section of the position of the laser illumination region 35 and the D 2 D 2' section of the laser illumination region 36 in FIG. 13 (A). Two types of lasers having different wavelengths are illuminated at the illumination regions (35 and 36) which are between the junction part and the sorting flow path. The sideward scattered lights generated when the cell passes through the illumination region are reflected downward by internal reflection at the reflection surfaces (180 and 181). The scattered lights emitted from the inside of the substrate by internal reflection is condensed by the light collecting blocks (182 and 183) made of transparent resin, and guided to the photodetectors (188, 189) by the light guides (184, 185) to be detected. In this case, a band pass filter with a wavelength range that transmits only the wavelength of the first laser light source 35-1, is installed in front of the photodetector (188) and a band pass filter with a wavelength range that transmits only the wavelength of the second laser light source 36-1, is installed in front of the photodetector (189), and whereby lights other than scattered light of each wavelength are removed. As shown in FIG. 5 (B), the time difference at which the time waveform of the two types of sideward scattering signals becomes maximum is calculated for the particles flowing in the flow path, and the flow rate of each particle is measured by dividing the distance between the illumination regions 35 and 36 by the time difference. FIG. 14 is a graph showing the histogram distribution of individual cells by measuring the flow rate.

2) Embodiment of Means for Solving the Problem on a Method for Analyzing the Gene of a Single Cell.

As the means for solving the problem on a method for analyzing the gene of a single cell, a method of forming droplets incorporating cells in emulsion, a method of dissolving cells in droplets in emulsion, a method of PCR reaction in droplets in emulsion, a method for collecting and concentrating fluorescent droplets in emulsion, a method for dispensing the collected droplets into a multiwell plate one by one, a method for destroying the droplets in the dispensed multiwell plate and mixing with another reaction reagent liquid, and a method for amplifying a whole gene and analyzing them with the next generation sequencer, will be explained.

Figure 6:
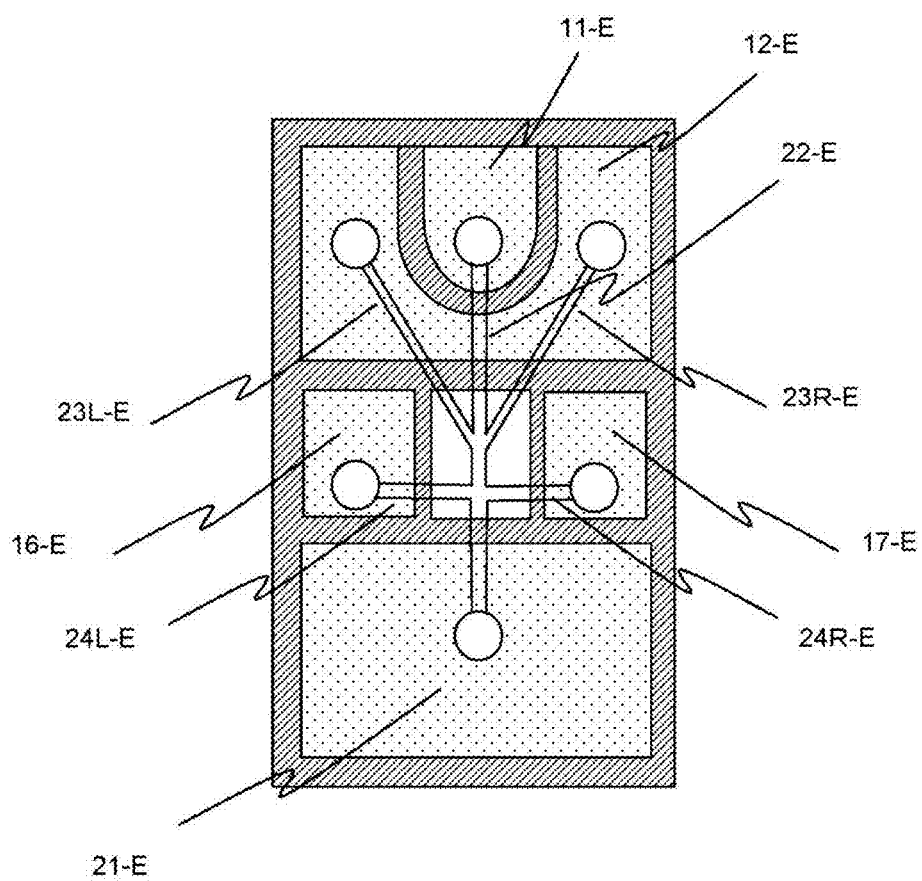
FIG. 6 is a disposable flow path cartridge for forming in-oil liquid droplets containing a cell.

FIG. 6 shows a disposable flow path cartridge for forming emulsion droplets incorporating cells in emulsion. It has almost the same structure as the cartridge of FIG. 2, but the role of each reservoir is different. In this cartridge, a sample liquid reservoir (first reservoir) 11-E containing cells to be taken into the droplet, a reaction reagent liquid reservoir (second reservoir) 12-E containing the PCR reaction reagent and cell lysis reagent, right-and-left emulsion oil reservoirs (third A reservoir) 16-E and (third B reservoir) 17-E, and a reservoir for forming droplets in emulsion (fourth reservoir) 21-E, are formed. Controlled air pressure is applied to the upper part of each reservoir and the size of in-oil liquid droplets can be adjusted by the air pressure of each reservoir. As an adjustment mechanism of the air pressure in the reservoirs, a combination of a compressor and an electropneumatic regulator is suitable, as shown in FIG. 18. The pressure adjustment range may be from 0.1 kPa to 30 kPa. It is possible to adjust the diameter size of in-oil liquid droplets from 20 µm to 100 µm by changing the pressure applied to the emulsion oil reservoirs (third A and B reservoirs) with respect to the pressure applied to the first reservoir and the second reservoir. However, the viscosity varies depending on the type of oil, and thus, it is necessary to control the air pressure for each type of oil, in order to obtain the desired size droplets. In order to take cells of about 10 µm in the droplets in emulsion, the size of liquid droplets is preferably 40 µm or more. The upper limit of the maximum size liquid droplets is determined by the size of the flow path.

Figure 7:
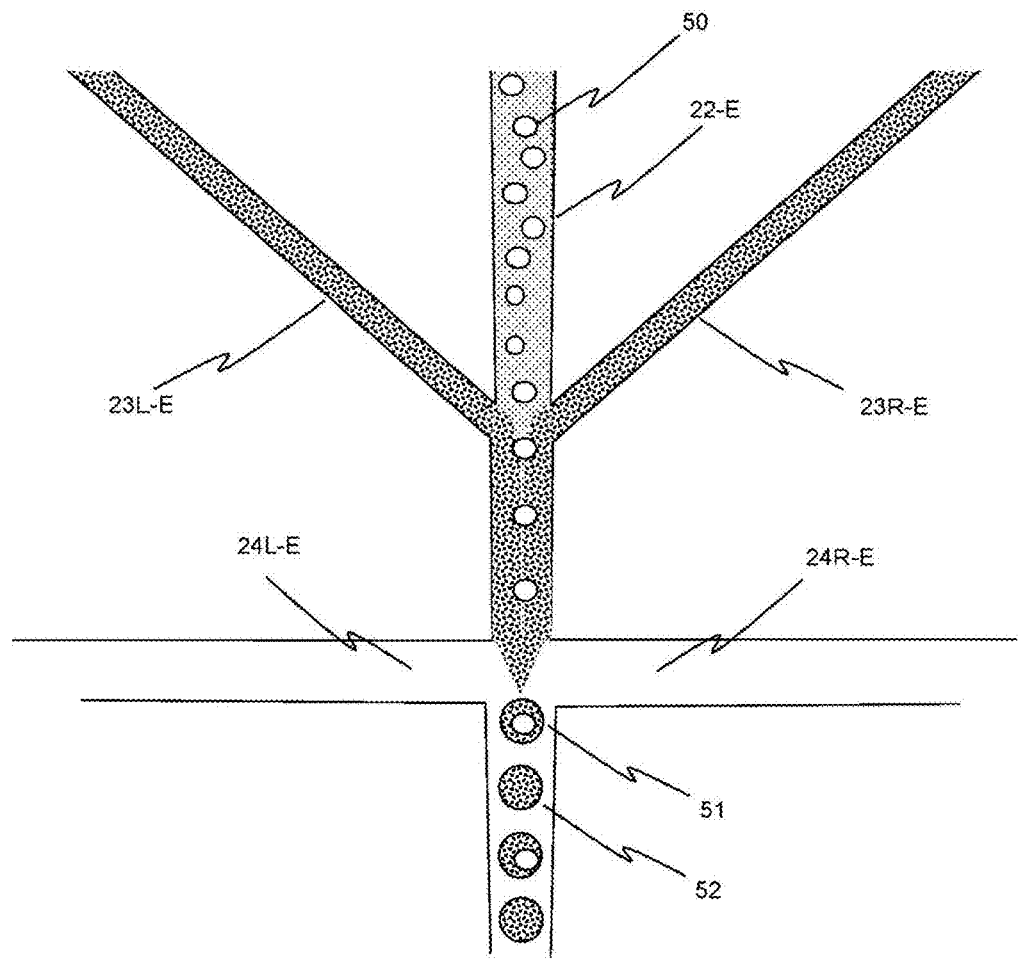
FIG. 7 is an illustration drawing of the flow path pattern of FIG. 6.

FIG. 7 shows flow paths in a micro flow path cartridge for forming the water-in-oil emulsion droplets. The sample liquid containing the cells 50 joins up with the flow paths 23L-E and 23L-E through which the reaction reagent liquid (PCR reaction reagent and cell lysis reagent) flows, and whereby the cells 50 aligned in a line, and then the oil joins thereto from the flow path 24L-E and the flow path 24R-E. The in-oil liquid droplets are formed after joining, in particular, two kinds of droplets 51 including cells and droplets 52 not including cells are formed.

Figure 8:
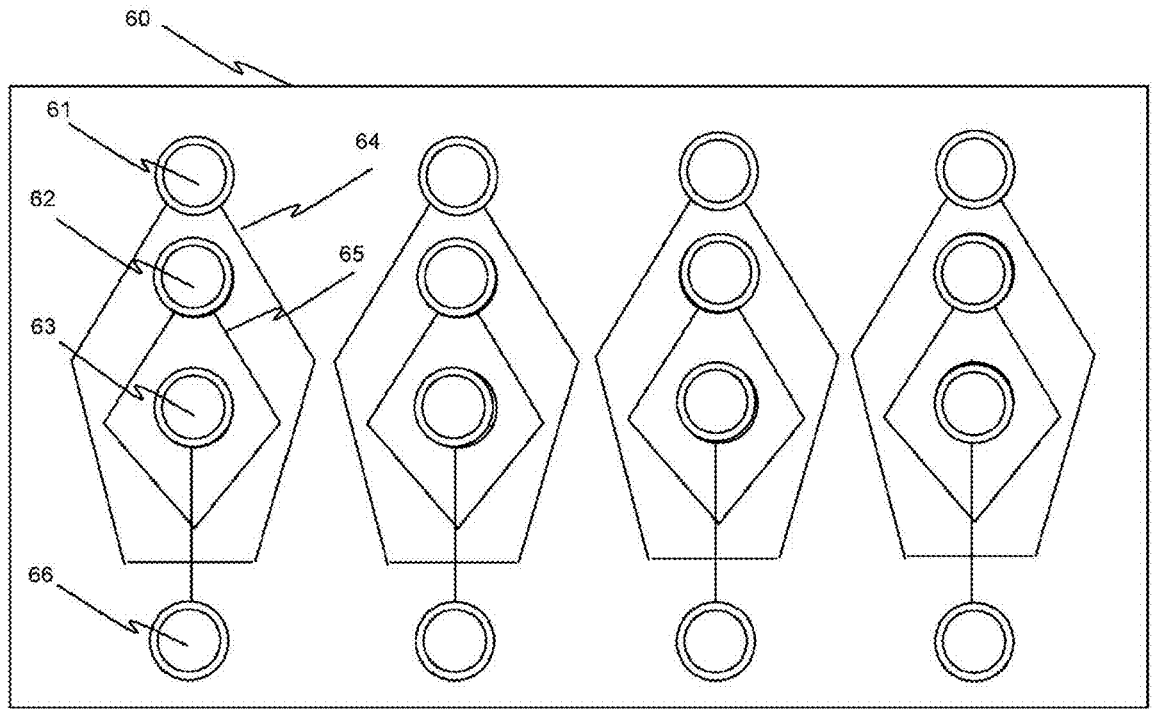
FIG. 8 is a top view of the disposable flow path cartridge wherein four in-oil liquid droplets containing a cell are simultaneously formed.

FIG. 8 shows a cartridge for forming emulsion in which four sample liquid reservoirs 63, four reagent reservoirs 62, and four oil reservoirs are formed. The particles in emulsion are formed by applying air pressure force to each reservoir. In the flow path cartridge, emulsions for four types of samples can be formed at once. As a type of oil capable of forming emulsion, there may be mentioned a fluorine-based oil or a mineral oil. The diameter size of the droplet is determined by the ratio of the flow rate of the liquid and the flow rate of the oil at the joint portion with the oil. When forming water-in-oil emulsion droplets containing a cell of about 10 µm in size one by one, it is preferable that the size of the liquid droplets is at least 40 µm or more. Further, in this case, the cross-sectional size of the flow path 22-E may be 100 µm width or less and 100 µm depth or less. However, when forming water-in-oil emulsion droplets incorporating spheroids, which is a mass of cells, having a size of about 100 the cross-sectional size of the flow path 22-E should be 200 µm width and 200 µm depth or more.

As a reagent for cell lysis, an enzyme such as Proteinase K that decomposes a cell membrane is added as a component. As a PCR reaction reagent, in addition to primers corresponding to a gene sequence to be detected, a polymerase, a TaqMan probe, or a fluorescent reagent such as a cyber green is added as a component. The cell lysis reaction is performed by allowing to stand for 12 hours at 36° C., when lysing cells with Proteinase K.

Next, for example, PCR reaction is performed by repeating a thermal cycle between temperatures of 60° C. and 95° C. for about 40 times, using a thermal cycler. After PCR reaction, liquid droplets having the desired gene sequence will have fluorescence.

In the next step, only the liquid droplets having fluorescence are sorted in the above flow path cartridge. The procedure is described in 1-5). As a result of this sorting, an emulsion containing 95% or more of liquid droplets having a target gene sequence is obtained.

Figure 9:
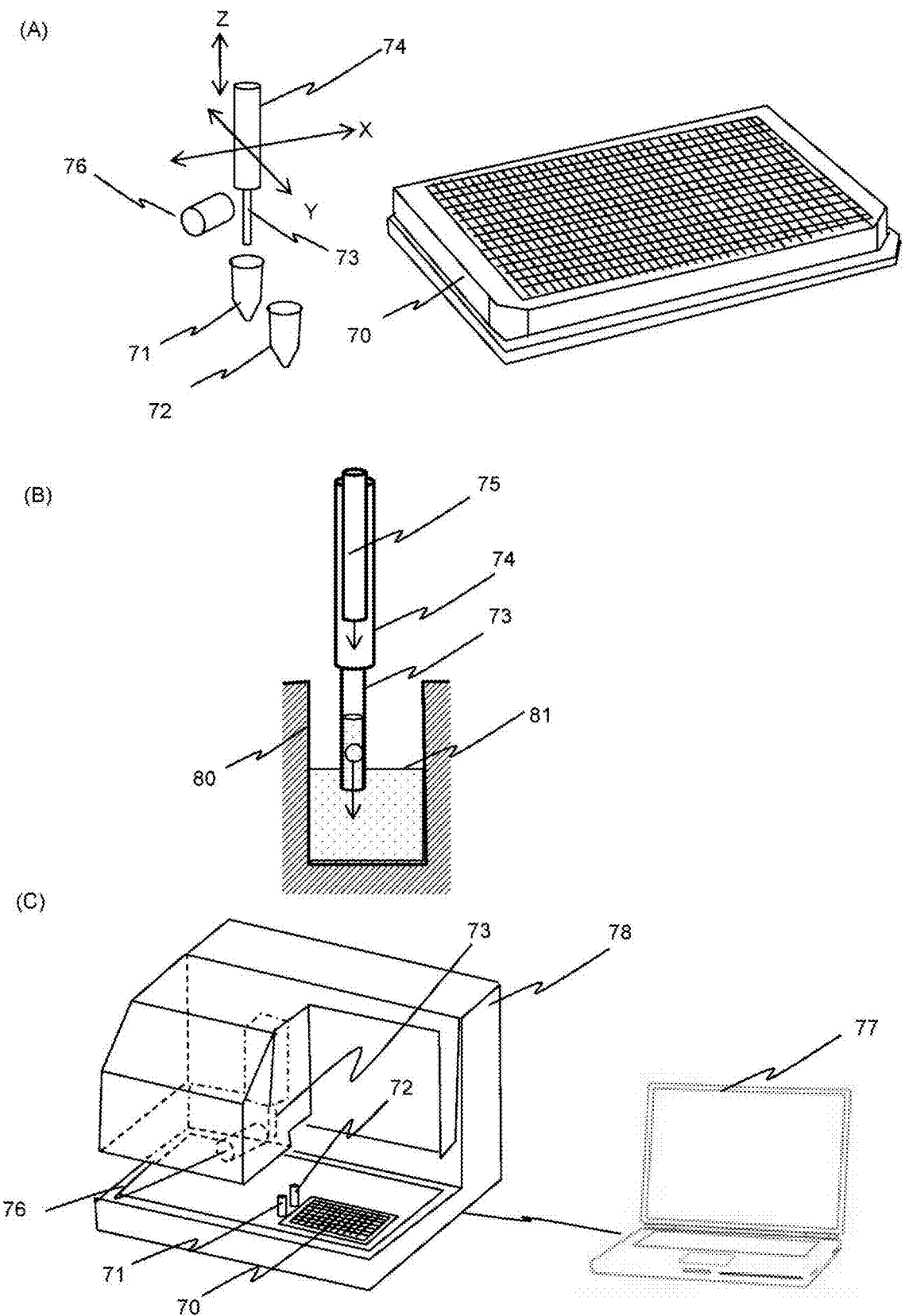
FIG. 9 is (A) a view showing a method for dispensing in-oil liquid droplets, (B) a view showing a discharge of in-oil liquid droplets from a dispensing pipette and (C) an external view of the apparatus.

Next, a means for dispensing these water-in-oil emulsion droplets on a multi-well plate one by one will be explained. FIG. 9 (A) schematically shows the means for dispensing emulsion droplets.

A reagent liquid to be reacted with the liquid droplet after dispensing is dispensed to the multiwell plate 70 to be dispensed in. This reagent liquid is, for example, an aqueous solution containing a reagent for amplifying the whole gene. The liquid droplets before dispensing are in the tube 71. A tip of a dispensing pipette 73, which is a transparent hollow pipe attached to the tip of a syringe pump 74 for controlling air pressure, is moved downward in the Z axis to the emulsion liquid in this tube 71. Next, the emulsion liquid is aspirated into the pipette 73 by pulling the syringe piston by the dispensing amount. After aspiration, the pipette 73 is moved upward in the Z axis and then an image of the entire dispensing amount in the pipette is obtained with a camera, and whereby it is judged whether or not there is one liquid droplet. If there is one liquid droplet, the pipette is moved to the well of the predetermined address of the multi-well plate. As shown in FIG. 9 (B), the dispensing pipette 73 is moved downward in the Z axis, and further moved below the upper surface 81 of the dispensed reaction reagent liquid. Then, the piston 75 of syringe pump is pushed out and the liquid droplet in the pipette is discharged. After discharge, the dispensing pipette is moved upward while pushing down the piston 75. As a result of image recognition within the dispensing pipette, if the number of droplets is zero or more than two, the dispensing pipette 73 returns back to the tube 71 and the emulsion liquid in the inside is discharged. Then, the emulsion liquid is aspirated again and dispensed only when there is only one droplet.

Figure 16:
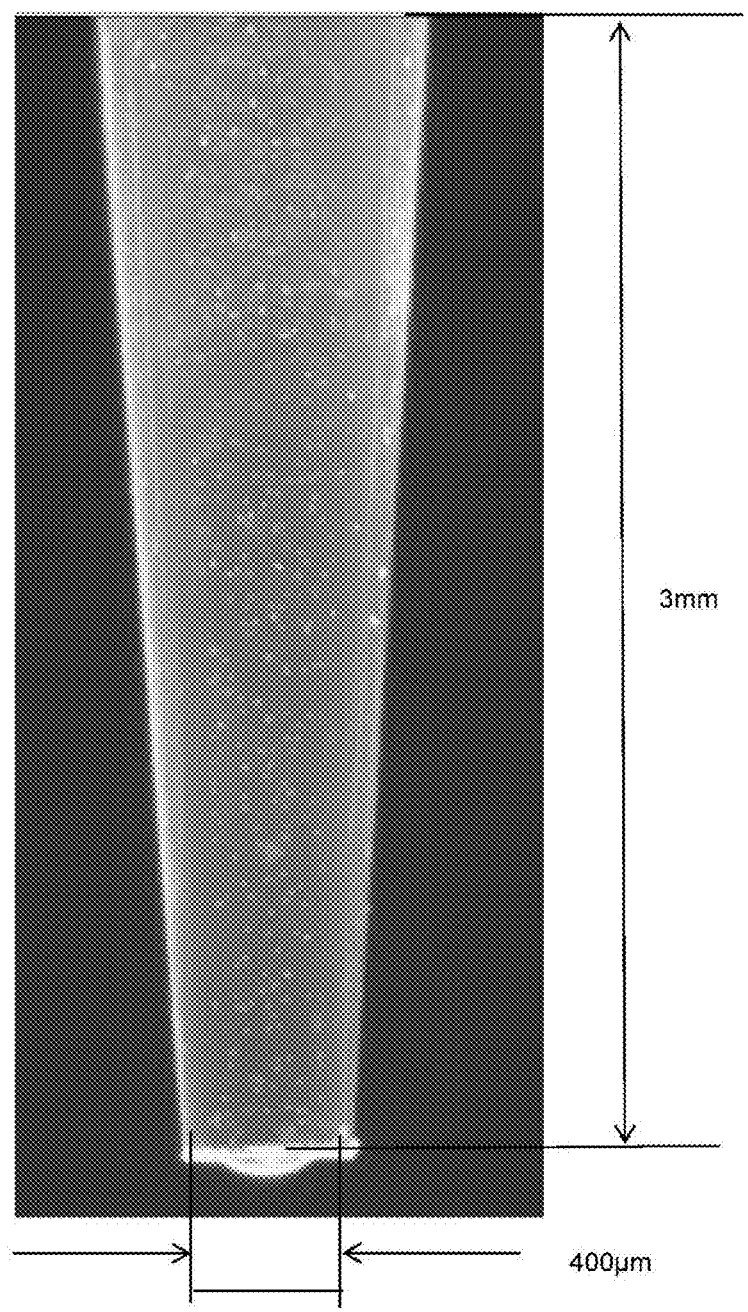
FIG. 16 is a camera image of particles with a diameter of 10 μm in the dispensing pipette.

In the case of 0.3 μL of the dispensing amount, if the inner diameter of the pipette is 400 μm, the aspiration may be performed up to 2.4 mm in the pipette. Next, it is considered whether or not the entire volume of 0.3 μL can be photographed with the image of one shot of the camera in focus. When a 1× objective lens is used, the depth of the field is 440 μm, and thus, it is possible to photograph with the entire inner diameter of 400 μm in the pipette in focus. Considering the breadth of the field of view, the field of view of 6.4 mm is covered in the case of ½ type camera, and therefore it is possible to shoot the entire 2.4 mm length in the pipette. Therefore, it can be recognized that it is possible to photograph the entirety of the dispense amount of 0.3 μL with one image shot. In connection to this, since the resolution of the image is 11 μm, the presence or absence of one cell and the number can be identified. An optimum size of the liquid droplets which takes one cell is 40 μm, and thus it is possible to sufficiently distinguish the presence or absence of liquid droplets and the number of liquid droplets in an emulsion. FIG. 16 shows an image of a standard particle with a size of 10 μm in the hollow pipette made of transparent resin having an inner diameter of 400 μm, which is obtained by a 1× objective lens and ½ type camera. Each of the particles can be distinguished and the length of the aspirated liquid is 2.4 mm or more.

In the above-described dispensing of liquid droplets in an emulsion, it is preferable to coat an inside of the dispensing pipette with a water repellent coating solution, in order to prevent adhesion of liquid droplets to the inner wall of the dispensing pipette. Further, the above dispenser can be used for dispensing cells in an aqueous solution. In this case, in order to prevent adhesion of cells to the inner wall of the dispensing pipette, it is preferable to coat the inside of the dispensing pipette with a hydrophilic coating solution.

In order to analyze the DNA of one cell contained in one liquid droplet in a multiwell plate in detail, it is preferable to determine the whole sequence with the next generation sequencer. For this sequence analysis, it is necessary to amplify a whole genome. A method for performing a whole genome amplification reaction by destroying the dispensed individual water-in-oil emulsion droplets and mixing an extracted DNA with a reaction reagent liquid for the whole genome amplification, will be described below. First of all, in order to extract the internal DNA by destroying individual liquid droplets, the method using centrifugation and diethyl ether described in Non-Patent literature 5 is applied. This method is applied to each liquid droplet one by one, and thus, the emulsion liquid dispensed one by one into a multiwell plate is transferred to a centrifuge tube, and the method is performed. Next, in order to perform the whole genome amplification reaction on the extracted DNA, for example, a whole genome amplification kit (SeqPlex DNA Amplification Kit; Sigma-Aldrich) for a next generation sequencer is used. This protocol is described in Non-Patent literature 6. Further, in the analysis of RNA, for example, a total RNA amplification kit (SeqPlex DNA Amplification Kit; Sigma-Aldrich) for the next generation sequencer is used. This protocol is described in Non-Patent literature 7.

Figure 17:
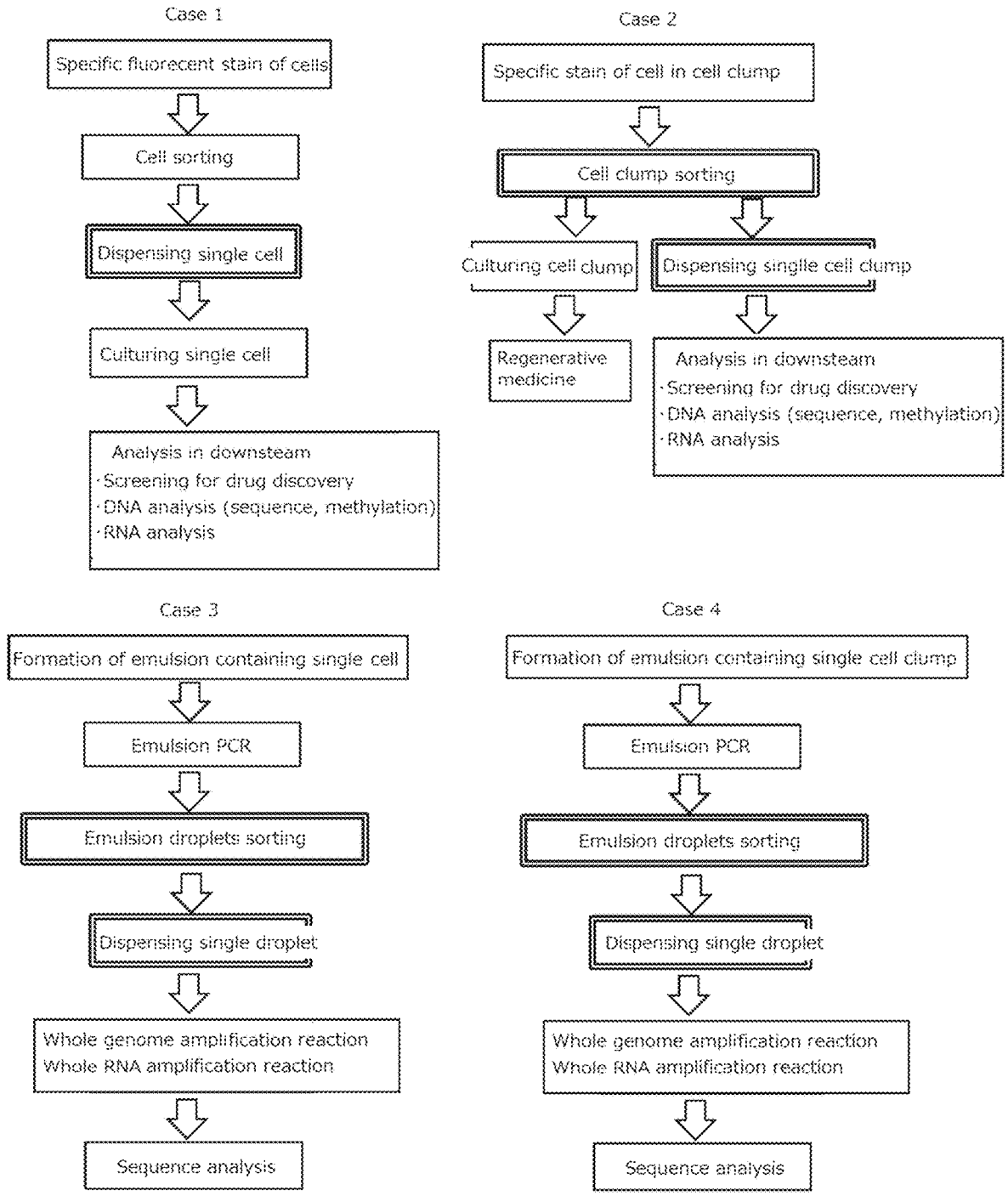
FIG. 17 is summarized flow charts of an analysis procedure of a single cell (case 1), an analysis procedure of a clump of cells (case 2), an analysis procedure of a liquid droplet containing a single cell in emulsion (case 3), and an analysis procedure of a liquid droplet containing a single clump of cells in emulsion (case 4).

In FIG. 17, analysis procedures related to the present invention are summarized. The analysis procedures are a single cell analysis (case 1), a single clump of cells analysis (case 2), liquid droplet in emulsion analysis containing a single cell (case 3), liquid droplet in emulsion analysis containing a single clump of cells (case 4). The means of the present invention is necessary for the procedure of each case. After the above amplification, the sequence analysis is carried out by the next generation sequencer.

INDUSTRIAL APPLICABILITY

In the apparatus for analyzing and separating particles of the present invention, it is possible to aseptically separate cells suitable for regenerative medicine. In addition, since the sample concentration can be easily regulated, the cell concentration in the sample can be adjusted. In addition, the apparatus for analyzing and separating particles is capable of easily sorting cell spheroids, or emulsions. Further, the differentiated cells can be easily purified by using the apparatus of the present invention. According to the present invention, the flow rate of a cell or clump of cells can be measured, and thus the cells or cell clumps can be sorted without using specific buffers. Furthermore, according to the gene analysis system or gene analysis method of the present invention, genes of a single cell or a single clump of cells (cell spheroid) can be analyzed without contamination.

Although the present invention has been described with reference to specific embodiments, various changes and modifications obvious to those skilled in the art are possible without departing from the scope of the appended claims.

REFERENCE SIGNS LIST

1 . . . Flow path substrate
2a . . . Reservoir
2b . . . Reservoir
3a . . . Reservoir cover
3b . . . Reservoir cover
4 . . . Flow path
5a . . . Sample liquid
5b . . . Sample liquid
6a . . . Air
6b . . . Air
8a . . . Hollow needle
8b . . . Hollow needle
9a . . . Syringe pump
9b . . . Syringe pump
10 . . . Outer frame of disposable flow path cartridge
11 . . . Reservoir for reserving sample liquid (sample reservoir: first reservoir)
11-e . . . Sample liquid containing particles to be taken in liquid droplets emulsion
12 . . . Reservoir for reserving sheath liquid (second reservoir)
12-E . . . Reagent for dissolving cells and reagent liquid containing PCR reaction reagent
13 . . . Main flow path of sample liquid and connection port
14 . . . Partition wall between sample liquid and sheath liquid
15L . . . Left connection port of sheath liquid with sheath flow path
15R . . . Right connection port of sheath liquid with sheath flow path
16 . . . Sorting liquid reservoir (third A reservoir)
16-E . . . Emulsion oil reservoir (third A reservoir)
17 . . . Collection reservoir (third B reservoir)
17-E . . . Emulsion oil reservoir (third B reservoir)
18 . . . Connection port of sorting liquid reservoir with sorting flow path
19 . . . Connection port of collection reservoir with sorting flow path
20 . . . Connection port of discharged liquid with main flow path
21 . . . Reservoir for reserving discharged liquid (fourth reservoir)
21-E . . . Reservoir for forming droplets in emulsion (fourth reservoir)

22 . . . Main flow path (first flow path)
22-E . . . Main flow path (first flow path)
23L . . . Left sheath flow path (second flow path)
23L-E . . . Left reagent flow path (second flow path)
23R . . . Right sheath flow path (third flow path)
23R-E . . . Right reagent flow path (third flow path)
24L . . . Sorting flow path of Push side of pulse flow (fourth flow path)
24L-E . . . Flow path for liquid droplets-forming oil (fourth flow path)
24R . . . Sorting flow path of Pull side of pulse flow (fifth flow path)
24R-E . . . Flow path for liquid droplets-forming oil (fifth flow path)
30 . . . Hollow needle for penetrating through cover of sample liquid reservoir
31 . . . Hollow needle for penetrating through cover of sheath liquid reservoir
32 . . . Hollow needle for penetrating through cover of sorting liquid reservoir
33 . . . Hollow needle for penetrating through cover of collection reservoir
34 . . . Hollow needle for penetrating through cover of discharged liquid reservoir
35 . . . First laser light or illumination region thereof
35-A . . . Scattered light signal generated when passing through the laser illumination region
36 . . . Second laser light which is different from first laser light or illumination region thereof
36-A . . . Scattered light signal generated when passing through the laser illumination region
35-1 . . . First laser light source
35-2 . . . Driver circuitry of laser
36-1 . . . Second laser light source
40 . . . Teflon (registered trademark) adapter of sample liquid reservoir
41 . . . Teflon (registered trademark) adapter of collection reservoir
50 . . . Cell
51 . . . Liquid droplets containing cell
52 . . . Liquid droplets not containing cell
60 . . . Flow path cartridge for forming water-in-oil emulsion droplets
61 . . . Oil reservoir for forming water-in-oil emulsion droplets
62 . . . Reagent reservoir
63 . . . Sample liquid reservoir
64 . . . Oil flow path for forming water-in-oil emulsion droplets
65 . . . Reagent flow path
65 . . . Reservoir for water-in-oil emulsion droplets
70 . . . Multiwell plate wherein water-in-oil emulsion droplets are dispensed
71 . . . Emulsion liquid containing liquid droplets before dispensing
72 . . . Oil liquid for washing
73 . . . Dispensing pipette (transparent hollow pipe)
74 . . . Air pressure syringe pump
75 . . . Piston portion of air pressure syringe pump
76 . . . Camera
77 . . . Dispenser-controlling PC
78 . . . Single particle dispenser
80 . . . Well in multiwell plate
90 . . . Positive pressure syringe pump
91 . . . Negative pressure syringe pump
92 . . . High speed electromagnetic valve
93 . . . High speed electromagnetic valve
100 . . . Electromagnetic actuator
101 . . . Electromagnetic actuator
110 . . . Elastic cover
111 . . . Elastic cover
151 . . . Objective lens
152 . . . Laser light
153 . . . Region between sorting flow paths 4-1 and 4-2
154,155,156 . . . Dichroic mirror
157,158,159 . . . Band pass filter
160 . . . Spatial filter for blocking transmissive laser light
161 . . . Photodiode
162,163 . . . Photomultiplier
164 . . . AD converter
169 . . . Control computer
170 . . . Driver circuitry for air pump 9A
171 . . . Driver circuitry for air pump 9B
172 . . . Driver circuitry of illuminated laser light source 35-1
180,181 . . . Reflecting surface
182,183 . . . Light collecting blocks made of transparent resin
184,185 . . . Light guides made of transparent resin
186 . . . Band pass filter with a wavelength range that transmits only the wavelength of the first laser light source 35
187 . . . Band pass filter with a wavelength range that transmits only the wavelength of the second laser light source 36
188,189 . . . Photodetector
200 . . . Electromagnetic valve
201 . . . Driver circuitry of electromagnetic valve
202 . . . Electropneumatic regulator
203 . . . Air buffer tank
204 . . . Compressor
205 . . . Filter for removing extraneous substances in gas
206 . . . Atmospheric suction pipe of compressor
301 . . . Driver circuitry for electromagnetic actuator
401 . . . Cover wherein hole open
402 . . . Cover for closing hole
403 . . . Pole
404 . . . Space inside reservoir
405 . . . Side wall

The invention claimed is:

1. A method for purifying cells to be collected using an apparatus for septical analyzing and separating particles, in an enclosed space,
wherein the apparatus for analyzing and separating particles is sealed, in an enclosed space, and comprises:
a disposable flow path cartridge in which a flow path is formed in a transparent substrate, wherein the disposable flow path cartridge itself is a closed system,
an illumination unit,
a detection unit,
a force generating unit,
wherein a sample liquid reservoir is connected to a first flow path;
a fourth branched flow path and a fifth branched flow path which are connected to opposite sides of the first flow path;
a third-A reservoir connected to the fourth branched flow path;
a third-B reservoir connected to the fifth branched flow path; and
a fourth reservoir connected to a downstream side of the first flow path, and
wherein the fourth reservoir is formed on the cartridge, and each reservoir is covered by a seal cover so that the inside of the each reservoir is sealed from the outside, wherein seal covers of the third-A reservoir for delivering a pulse flow and the third-B reservoir for collecting the particles are stretchable and deformable membranes;

actuators which externally apply a mechanical force to the seal covers to displace the seal covers, and a sorting unit comprising the actuators and the seal covers, wherein the sorting unit is configured to sort the particles by generating the pulse flow in the branched flow paths through pushing down of the seal cover of the third-A reservoir, and pulling up of the seal cover of the third-B reservoir using the actuators, when the particles pass through a sorting region;

illuminating particles in a sample liquid flowing through the flow path;

detecting particles of interest by detecting scattered light or fluorescence generated from the particles when the particle is illuminated;

identifying the particles based on its signal intensity;

delivering a pulse flow to the fourth branched flow path for changing a flow direction to the particles which flow in the flow path of the cartridge based on the signal from the detection unit;

changing a particle course through the pulse flow generated by the force generating unit, which flows from the fourth branched flow path to a direction of the fifth branched flow path, to sort and collect the particles; and reserving particles in the fourth reservoir which are not sorting;

wherein the method is further characterized in that 20% or less cells to be uncollected are mixed in the cells to be collected, the cells to be collected are differentiated from the cells to be uncollected, and the cells to be uncollected are removed, wherein the force created by a force generating unit comprising a constant air pump and an electromagnetic valve is applied to the cells to be uncollected so as to change the course thereof and a force created by constant air pump in combination with the electromagnetic valve is not applied to the cells to be collected so as not to change the course thereof based on the signal from the detection unit, whereby the cells to be uncollected are removed from the cells to be collected contained in the fourth reservoir so as to recover a cell liquid and increase a collection rate of the cells to be collected relative to a collection rate of the cells to be uncollected.

2. A method for purifying cells to be collected according to claim 1, wherein the recovered cell liquid is subjected to the same treatment for removing the cells to be uncollected repeatedly.

3. A method for purifying cells to be collected using an apparatus, wherein the apparatus for septical analyzing and separating particles, in an enclosed space comprises:

a disposable flow path cartridge in which a flow path is formed in a transparent substrate, wherein the disposable flow path cartridge itself is a sealed system, an illumination unit, a detection unit, a force generating unit, wherein a sample liquid reservoir is connected to a first flow path;

a fourth branched flow path and a fifth branched flow path which are connected to opposite sides of the first flow path;

a third-A reservoir connected to the fourth branched flow path;

a third-B reservoir connected to the fifth branched flow path; and a fourth reservoir connected to a downstream side of the first flow path, and wherein the fourth reservoir is formed on the cartridge, and each reservoir is covered by a seal cover so that the inside of each reservoir is sealed from the outside, wherein the seal covers of the third-A reservoir for delivering a pulse flow and the third-B reservoir for collecting the particles are stretchable and deformable membranes, and actuators which externally apply a mechanical force to the seal covers to displace the seal covers, and a sorting unit comprising the actuators and the seal covers, wherein the sorting unit is configured to sort the particles by generating the pulse flow in the branched flow paths through pushing down of the seal cover of the third-A reservoir, and pulling up of the seal cover of the third-B reservoir using the actuators, when the particles pass through a sorting region and wherein a flow path width and a flow path depth of the flow paths are each 150 µm or more, and a size of an illumination laser beam in the direction of flow path width is 100 µm or more;

illuminating particles in a sample liquid flowing through the flow path;

detecting particles of interest by detecting scattered light or fluorescence generated from the particles when the particle is illuminated;

identifying the particles based on its signal intensity;

delivering a pulse flow to the fourth branched flow path for changing a flow direction to the particles which flow in the flow path of the cartridge based on the signal from the detection unit;

changing a particle course through the pulse flow generated by the force generating unit, which flows from the fourth branched flow path to a direction of the fifth branched flow path, to sort and collect the particles; and reserving particles in the fourth reservoir which are not sorting;

wherein the method is further characterized in that 20% or less, cells to be uncollected are mixed in the cells to be collected, the cells to be collected are differentiated from the cells to be uncollected, and the cells to be uncollected are removed, wherein a force created by a force generating unit comprising a constant air pump and an electromagnetic valve is applied to the cells to be uncollected so as to change the course thereof and a force created by constant air pump in combination with the electromagnetic valve is not applied to the cells to be collected so as not to change the course thereof based on the signal from the detection unit, whereby the cells to be uncollected are removed from the cells to be collected contained in the fourth reservoir so as to recover a cell liquid and increase a collection rate of the cells to be collected relative to a collection rate of the cells to be uncollected.

4. A method for purifying cells to be collected according to claim 3, wherein the recovered cell liquid is subjected to the same treatment for removing the cells to be uncollected repeatedly.

5. The method of claim 1, wherein the apparatus further comprises:
- a unit which equalizes air pressure comprising an in-device air pressure control system, the unit in each reservoir with the air pressure of the in-device air pressure control system, and a stream of the flow path in the cartridge is controlled by controlling the air pressure in each reservoir through each in-device air pressure control system.

* * * * *